United States Patent
Doller et al.

(10) Patent No.: US 12,029,712 B2
(45) Date of Patent: *Jul. 9, 2024

(54) DEUTERATED ANALOGS OF D-SERINE AND USES THEREOF

(71) Applicant: Sun Pharmaceutical Industries, Inc., Princeton, NJ (US)

(72) Inventors: Dario Doller, Sparta, NJ (US); Christopher L. Brummel, Marlborough, MA (US); Julie F. Liu, Lexington, MA (US); Roger D. Tung, Lexington, MA (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 222 days.

This patent is subject to a terminal disclaimer.

(21) Appl. No.: 16/884,652

(22) Filed: May 27, 2020

(65) Prior Publication Data
US 2020/0390732 A1 Dec. 17, 2020

Related U.S. Application Data

(63) Continuation of application No. 16/459,916, filed on Jul. 2, 2019, now Pat. No. 10,668,036, which is a continuation of application No. PCT/US2018/062263, filed on Nov. 21, 2018.

(60) Provisional application No. 62/755,157, filed on Nov. 2, 2018, provisional application No. 62/636,427, filed on Feb. 28, 2018, provisional application No. 62/636,081, filed on Feb. 27, 2018, provisional application No. 62/590,109, filed on Nov. 22, 2017.

(51) Int. Cl.
| | | |
|---|---|---|
| A61K 31/197 | (2006.01) | |
| A61K 9/00 | (2006.01) | |
| A61K 31/198 | (2006.01) | |
| A61K 45/06 | (2006.01) | |
| A61P 25/18 | (2006.01) | |

(52) U.S. Cl.
CPC .......... *A61K 31/197* (2013.01); *A61K 9/0053* (2013.01); *A61K 31/198* (2013.01); *A61K 45/06* (2013.01); *A61P 25/18* (2018.01)

(58) Field of Classification Search
None
See application file for complete search history.

(56) References Cited

U.S. PATENT DOCUMENTS

| | | |
|---|---|---|
| 4,582,931 A | 4/1986 | Grabowski et al. |
| 5,845,286 A | 12/1998 | Javitt et al. |
| 6,221,335 B1 | 4/2001 | Foster |
| 6,228,875 B1 | 5/2001 | Tsai et al. |
| 6,258,605 B1 | 7/2001 | Chace |
| 6,440,710 B1 | 8/2002 | Keinan et al. |
| 6,603,008 B1 | 8/2003 | Ando et al. |
| 7,517,990 B2 | 4/2009 | Ito et al. |
| 7,884,124 B2 | 2/2011 | Heffernan et al. |
| 8,492,418 B2 | 7/2013 | Woods |
| 9,040,581 B1 | 5/2015 | Kumar |
| 9,687,460 B2 | 6/2017 | Heresco-Levy |
| 10,668,036 B2 | 6/2020 | Doller et al. |
| 2002/0035145 A1* | 3/2002 | Tsai ..................... A61K 31/198 514/472 |
| 2002/0183390 A1 | 12/2002 | Javitt |
| 2007/0082929 A1 | 4/2007 | Gant et al. |
| 2007/0197695 A1 | 8/2007 | Potyen et al. |
| 2008/0103122 A1 | 5/2008 | Veltri |
| 2009/0176715 A1 | 7/2009 | Javitt et al. |
| 2014/0187597 A1* | 7/2014 | Heresco-Levy ..... A61K 31/198 514/380 |
| 2017/0157066 A1 | 6/2017 | Javitt |
| 2017/0326137 A1* | 11/2017 | Heresco-Levy ....... A61K 45/06 |
| 2022/0313640 A1 | 10/2022 | Doller et al. |

FOREIGN PATENT DOCUMENTS

| | | |
|---|---|---|
| JP | 2002/511409 | 4/2002 |
| WO | WO 1995/26325 | 10/1995 |
| WO | WO 1999/52519 | 10/1999 |
| WO | WO 2007/118651 | 10/2007 |
| WO | WO 2012/019106 | 2/2012 |
| WO | WO 2014/205074 | 12/2014 |
| WO | WO 2015/160470 | 10/2015 |
| WO | WO-2015160470 A2 * | 10/2015 |
| WO | WO 2017/098029 | 6/2017 |
| WO | WO 2017/210097 | 12/2017 |
| WO | WO 2019/104179 | 5/2019 |
| WO | WO 2020/243650 | 12/2020 |

OTHER PUBLICATIONS

STN RN 1414348-52-9 published in the database Dec. 12, 2012 (Year: 2012).*
STN RN 103292-62-2 published in the database Jul. 19, 1986. (Year: 1986).*
Kantrowitz et al. Schizophrenia Research, Aug. 2010, (Year: 2010).*
Blake et al. Journal of Pharmaceutical Sciences Mar. 1975 367 (in the IDS); (Year: 1975).*
Concert Pharma et al. Internet Citation (in the IDS), 2007; (Year: 2007).*
Kinoshita et al. Analytical Biochemistry 432 (2013) 124-130; (Year: 2013).*
Ito et al. FEBS Journal 279 (2012) 612-624. (Year: 2012).*
Tsai et al. Biol. Psychiatry 1998, 44:1081-1089. (Year: 1998).*

(Continued)

*Primary Examiner* — Jeffrey S Lundgren
*Assistant Examiner* — Michael J Schmitt
(74) *Attorney, Agent, or Firm* — Fish & Richardson P.C.

(57) ABSTRACT

This disclosure relates to deuterated D-serine, pharmaceutically acceptable salts thereof, analogs and prodrugs thereof, pharmaceutical compositions thereof, and methods of use.

25 Claims, 12 Drawing Sheets

(56) References Cited

OTHER PUBLICATIONS

U.S. Appl. No. 16/766,194, filed May 21, 2020, Doller et al.
Axelsson et al., "Versatile Synthesis of Stereospecifically Labelled D-Amino Acids via Labelled Aziridines-Preparation of (2R,3S)-[3-2H and (2R,3R)-[2,3-2H,]-Serine; (2S,2'St3S,3'S)-[3,3'-2H2]- and (2S,2'S,3R,3'R)-[2,2',3,3'-2Hq]-Cystine; and (2S,3S)-[3-*H and (2S. 3R)-[2,3-2H2]-p-Chloroalanine," J. Chem. Soc. Perkin Trans. 1, 1994, 807-815.
Baggott et al., "Metabolism of methionine derived from deuterated serine infused in a human," Am J Clin Nutr, 2001, 74:701-703.
Baillie et al., "The Use of Stable Isotopes in Pharmacological Research," Pharmacological Reviews, 1981, 33(2):81-132.
Blake et al., "Studies with Deuterated Drugs," J Pharm Sci, 1975, 64:367-391.
Browne, T. R., "Stable Isotope Techniques in Early Drug Development: An Economic Evaluation," J. Clin. Pharmacol., 1998, 38:213-220.
Cherrah et al., "Study of Deuterium Isotope Effects on Protein Binding by Gas Chromatography/Mass Spectrometry. Caffeine and Deuterated Isotopomers," Biomedical and Environmental Mass Spectrometry, 1987, 14:653-657.
Cho et al., "Low D-serine levels in schizophrenia: A systematic review and meta-analysis," Neuroscience Letters, 2016, 634:42-51.
Concert Pharmaceuticals et al., "Precision Deuterium Chemistry Backgrounder," Concert Pharmaceuticals Inc., 2007, 1-6.
Denu et al., "Intrinsic Primary, Secondary, and Solvent Kinetic Isotope Effects on the Reductive Half-Reaction of D-Amino Acid Oxidase: Evidence against a Concerted Mechanism1," Biochemistry, 1994, 33:4001-4007.
Denu et al., "pH and Kinetic Isotope Effects on the Reductive Half-Reaction of D-Amino Acid Oxidase," Biochemistry, 1992, 31:8207-8215.
Dyck et al., "Effects of Deuterium Substitution on the Catabolismof β-Phenylethylamine: An In Vivo Study," Journal of Neurochemistry, 1986, 46(2): 399-404.
Fisher et al., "The Complexities Inherent in Attempts to Decrease Drug Clearance by Blocking Sites of CYP-Mediated Metabolism," Curr. Opin. Drug Discov. Devel., 2006, 9(1):101-109.
Foster et al., "Deuterium Isotope Effects in Studies of Drug Metabolism," Trends in Pharmacological Sciences, 1984, 5: 524-527.
Foster et al"Deuterium Isotope Effects in the Metabolism of Drugs and Xenobiotics: Implications for Drug Design," Advances in Drug Research, 1985, 14:1-40.
Fukuto et al., Determination of the Mechanism of Demethylenation of (Methylenedioxy)phenyl Compounds by Cytochrome P450 Using Deuterium Isotope Effects, J Med Chem, 1991, 34:2871-2876.
Ganote et al., "The Nature of D-Serine-Induced Nephrotoxicity," American Journal of Pathology, 1974, 77:269-282.
Gouyette, A., "Synthesis of Deuterium-labelled Elliptinium and its Use in Metabolic Studies," Biomedical and Environmental Mass Spectrometry, 1988, 15: 243-247.
Harbeson et al., "Deuterium Medicinal Chemistry: A New Approach to Drug Discovery and Development," Medchem News, 2014, No. 2:8-22.
Haskins, N. J., "The Application of Stable Isotopes in Biomedical Research," Biomedical Mass Spectrometry, 9(7): 269-277 (1982).
Honma S., et al., "The Metabolism of Roxatidine Acetate Hydrochloride," Drug Metabolism and Disposition, 15(4): 551-559 (1987).
Ito et al., "Role of zinc ion for catalystic activity in D-Serine dehydratase from *Saccharomces cerevisiae*: Role of zinc in Eukaryotic D-serine dehydratase," FEBS Journal, 2012, 279(4):612-624.
Kantrowitz et al., "D-serine for the treatment of negative symptoms in individuals at clinical high risk of schizophrenia: a pilot, double-blind, placebo-controlled, randomised parallel group mechanistic proof-of-concept trial," Lancet Psychiatry, 2015, 2:403-412 (Correction).
Kantrowitz et al., "D-serine for the treatment of negative symptoms in individuals at clinical high risk of schizophrenia: a pilot, double-blind, placebo-controlled, randomised parallel group mechanistic proof-of-concept trial," Lancet Psychiatry, 2015, 2:403-412.
Kantrowitz et al., "High dose D-serine in the treatment of schizophrenia," Schizophr Res., 2010, 121(1-3):125-130.
Kinoshita et al., "A surrogate analyte method to determine D-serine in mouse brain using liquid chromatography—tandem mass spectrometry," Analytical Biochemistry, 2013, 432: 124-130.
Kushner, D.J. et al., "Pharmacological Uses and Perspectives of Heavy Water and Deuterated Compounds," Can. J. Physiol. Pharmacol., 1999, 77:79-88.
Lane et al., "Sarcosine or D-Serine Add-on Treatment for Acute Exacerbation of Schizophrenia," Arch Gen Psychiatry, 2005, 62:1196-1204.
Menniti et al., "Allosteric Modulators for the Treatment of Schizophrenia: Targeting Glutamatergic Networks," Curr Top Med Chem., 2013, 13(1):26-54.
Nair et al., "A simple practice guide for dose conversion between animals and human," J. Basic Clin. Pharma., 2016, 7:27-31.
Orozco-Ibarra et al., "Evaluation of oxidative stress in d-serine induced nephrotoxicity," Toxicology, 2007, 229:123-135.
PCT International Search Report and Written Opinion in International Appln. No. PCT/US2018/062263, dated Apr. 8, 2019, 134 pages.
Pieniaszek, H. J., et al., "Moricizine Bioavailability via Simultaneous, Dual, Stable Isotope Administration: Bioequivalence Implications," J. Clin. Pharmacol, 1999, 39: 817-825.
Pollegioni et al., "Physiological functions of D-amino acid oxidases: from yeast to humans," Cell. Mol. Life Sci., 2007, 64(1373-1394.
Russak et al., "Impact of Deuterium Substitution on the Pharmacokinetics of Pharmaceuticals," Annals of Pharmacotherapy, 2019, 53(2):211-216.
Schell et al., "D-Serine as a Neuromodulator: Regional and Developmental Localizations in Rat Brain Glia Resemble NMDA Receptors," The Journal of Neuroscience, Mar. 1, 1997, 17(5):1604-1615.
Tonn et al., "Simultaneous Analysis of Diphenhydramine and a Stable Isotope Analog (2H10) Diphenhydramine Using Capillary Gas Chromatography with Mass Selective Detection in Biological Fluids from Chronically Instrumented Pregnant Ewes," Biological Mass Spectrometr, 1993, 22:633-642.
Tsai et al., "D-serine added to antipsychotics for the treatment of schizophrenia," Biol. Psychiarty, 1998, 44:1081-1089.
Weiser et al., "A Multicenter, Add-On Randomized Controlled Trial of Low-Dose d-Serine for Negative and Cognitive Symptoms of Schizophrenia," J. Clin. Psychiatry, 2012. 73(6):e728-e734.
Williams et al., "D-Serine-induced nephrotoxicity: possible interaction with tyrosine metabolism," Toxicology, 2004, 201:231-238.
Wolen, R. L., "The Application of Stable Isotopes to Studies of Drug Bioavailability and Bioequivalence," J. Clin. Pharmacol., 1986, 26:419-424.
"Concert Pharmaceuticals Announces Results from CTP-692 Phase 2 Trial in Patients with Schizophrenia" dated Feb. 1, 2021.
Fernandez et al., "Scales to assess psychosis in parkinson's disease: Critique and recommendations," Movement Disorders, Jan. 2008, 23(4):484-500.
Gelfin et al. "D-serine adjuvant treatment alleviates behavioural and motor symptoms in Parkinson's disease," International Journal of Neuropsychopharmacology, 2012, 15:543-549.
Voss et al., "Performance of a shortened Scale for Assessment of Positive Symptoms for Parkinson's disease psychosis," Parkinsonism & Relat. Disord., 2013, 19(3):295-299.

* cited by examiner

Urea nitrogen reference range from 9-18.6

Creatinine reference range from 0.2-0.5

Urea nitrogen reference range from 9-18.6

Creatinine reference range from 0.2-0.5

DEUTERATED ANALOGS OF D-SERINE AND USES THEREOF

BACKGROUND OF THE INVENTION

N-methyl-D-aspartate receptor (NMDA receptor or NMDAR) is a glutamate receptor and ion channel in nerve cells. Activation of NMDAR allows positively charged ions to flow through the membrane. NMDA receptors play a role in physiological processes affecting memory and mood. See e.g., Nicholls et al., Neuron, 2008, 58(1):104-17. Binding of an agonist (such as N-methyl-D-aspartate or glutamate) and a co-agonist (such as glycine or D-serine) is required for NMDAR activation.

Agents that modulate NMDA receptors have been reported to be useful in a variety of therapeutic applications. For example, memantine is used to treat Alzheimer's disease and Lewy Body Dementia. However, treatment with NMDA modulators can have side effects such as sedation and hallucinations.

Anti-NMDAR encephalitis is an autoimmune encephalitis characterized by the presence of antibodies against synaptic NMDAR. Anti-NMDAR encephalitis (also known as NMDA receptor antibody encephalitis or NMDAR encephalitis) has become the most common and best characterized antibody-defined autoimmune neuronal disorder. The encephalitis associated with antibodies against NMDAR predominantly affects children and young adults, occurs with or without tumor association, responds to treatment, but can relapse. The exact incidence of anti-NMDAR encephalitis is unknown. Due to the rareness of the syndrome and the varied clinical presentations, anti-NMDAR syndrome may be misdiagnosed and under-recognized.

Schizophrenia is a chronic and devastating neuropsychiatric disorder that is ranked as a leading cause of disability worldwide. The disease afflicts nearly 1% of the world's population, affecting both men and women equally, and striking all ethnic and socioeconomic groups with a similar level of prevalence. The illness is characterized by multiple symptoms that are categorized into three clusters known as positive symptoms (hallucinations and delusional behaviors), negative symptoms (anhedonia, social withdrawal and apathy), and cognitive dysfunction (diminished capacity for learning, memory, and executive function). Currently available antipsychotic drugs exhibit efficacy for positive symptoms, but have been limited in their capacity to treat negative symptoms and cognitive deficits.

D-serine occurs naturally in the human body, although in much smaller amounts than L-serine. Only L-serine is found in proteins.

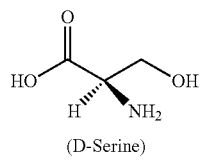

(D-Serine)

D-serine is an agonist of NMDA receptors. Academic studies have demonstrated that oral dosing of D-serine can result in dose-dependent improvement in positive, negative, and cognitive symptoms in schizophrenic patients when added to D2 antipsychotics (antipsychotic drugs that bind to and inhibit or block the activation of dopamine D2 receptors). However, preclinical studies have demonstrated that administration of D-serine can cause nephrotoxicity in rats. In addition, in some patients who received high doses of D-serine, clinical findings suggesting renal impairment were observed. As a result, the clinical development of D-serine has historically been limited.

There remains a need for improved treatments for NMDAR encephalitis and neurological conditions mediated by the NMDAR, including schizophrenia.

SUMMARY OF THE INVENTION

It has now been found that deuterated forms of D-serine (D-D-serine) may have advantageous properties, including reduced nephrotoxicity, relative to D-serine. Further, deuterated D-serine has the potential to restore NMDA receptor activity in key disease-related areas of the brain.

In one aspect, this invention relates to deuterated forms of D-serine, pharmaceutically acceptable salts thereof, analogs and prodrugs thereof, pharmaceutical compositions thereof, and methods of use.

In one aspect, the invention provides a pharmaceutical composition comprising a compound of Formula I:

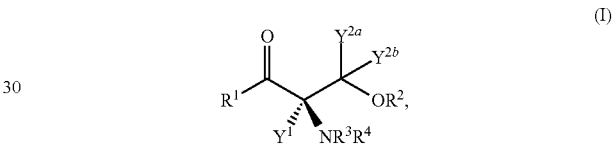

wherein
$R^1$ is —OH, —OD, —O—$C_{1-4}$ alkyl, or an amino acid residue;
$R^2$ is H, D, —$C_{1-4}$ alkyl, —C(O)—$C_{1-6}$ alkyl, or —C(O)—$C_{1-6}$ hydroxyalkyl;
$R^3$ is H, D, or an amino acid residue;
$R^4$ is H or D;
each of $Y^1$, $Y^{2a}$ and $Y^{2b}$ is independently H or D, provided that at least one of $Y^1$, $Y^{2a}$ and $Y^{2b}$ is D; wherein each position designated specifically as deuterium has at least 50.1% incorporation of deuterium;

or a pharmaceutically acceptable salt thereof;
and a pharmaceutically acceptable carrier.

In certain embodiments, in the compound of Formula I, $R^1$ or $R^3$ is a D-D-serine residue (a residue of deuterated D-serine).

In certain embodiments, the compound is a compound of Formula II:

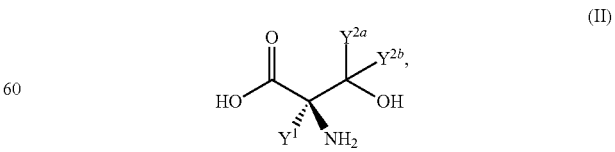

wherein each of $Y^1$, $Y^{2a}$ and $Y^{2b}$ is independently H or D, provided that at least one of $Y^1$, $Y^{2a}$ and $Y^{2b}$ is D;

or a pharmaceutically acceptable salt thereof.

In certain embodiments, the compound is selected from Compound 100 and Compound 103:

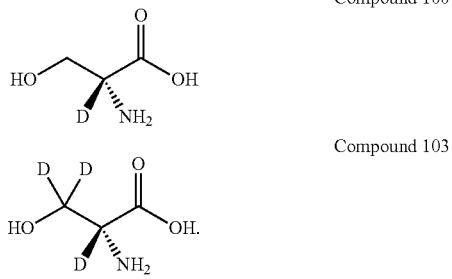

This invention also provides the use of such compounds and compositions in methods of treating diseases and conditions that are beneficially treated by administering a modulator of N-methyl-D-aspartate (NMDA) receptor function. Some exemplary embodiments include a method of treating a disease or condition selected from epilepsy, NMDAR encephalitis, Parkinson's disease, cognitive deficits in Parkinson's disease, Alzheimer's disease, mild cognitive impairment, amyotrophic lateral sclerosis (ALS), Huntington's disease, schizophrenia (including positive, cognitive, and/or negative symptoms of schizophrenia, as well as prodromal schizophrenia), bipolar disorder, bipolar mania, bipolar depression, treatment-refractory depression, cognitive deficits in depression, major depressive disorder, generalized anxiety disorder, major depressive disorder with mixed features, and cognition deficits associated with diseases or conditions such as Huntington's disease, subjective cognitive decline, traumatic brain injury, Lewy Body Dementia, the method comprising the step of administering to a subject in need thereof an effective amount of a compound or pharmaceutical composition of the present invention.

This invention also provides a method of treating schizophrenia (including positive, negative, and/or cognitive symptoms of schizophrenia), the method comprising administering to a subject in need thereof an effective amount of a compound or pharmaceutical composition of the present invention.

Further aspects and embodiments of the invention are also disclosed herein.

DETAILED DESCRIPTION OF THE INVENTION

Figure 1:
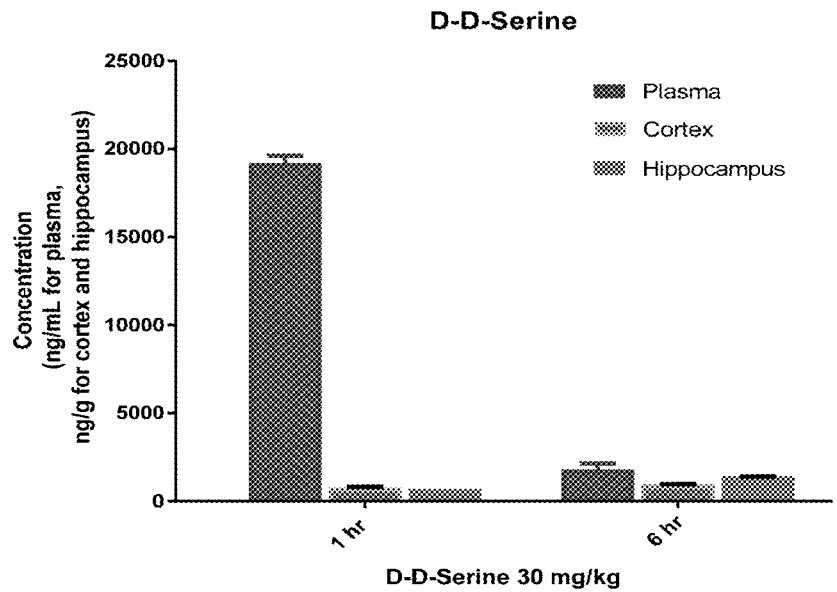
FIG. 1 is a graph showing the concentration of Compound 100 in rat plasma, hippocampus, and cortex after administration of a single dose of 30 mg/kg.

In one aspect, this invention relates to deuterated forms of D-serine, pharmaceutically acceptable salts thereof, analogs and prodrugs thereof, pharmaceutical compositions thereof, and methods of use.

In one aspect, the invention provides a compound of Formula I:

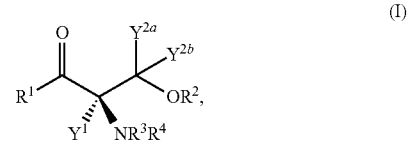

wherein
$R^1$ is —OH, —OD, —O—$C_{1-4}$ alkyl, or an amino acid residue;
$R^2$ is H, D, —$C_{1-4}$ alkyl, —C(O)—$C_{1-6}$ alkyl, or —C(O)—$C_{1-6}$ hydroxyalkyl;
$R^3$ is H, D, or an amino acid residue;
$R^4$ is H or D;
each of $Y^1$, $Y^{2a}$ and $Y^{2b}$ is independently H or D, provided that at least one of $Y^1$, $Y^{2a}$ and $Y^{2b}$ is D; wherein each position designated specifically as deuterium has at least 50.1% incorporation of deuterium;
or a pharmaceutically acceptable salt thereof.

In certain embodiments, each position designated specifically as deuterium has at least 90% incorporation of deuterium.

In certain embodiments, in the compound of Formula I, $R^1$ or $R^3$ is a D-D-serine residue (a residue of deuterated D-serine). When $R^1$ or $R^3$ is a D-D-serine residue, the compound of Formula I is a dipeptide; when both $R^1$ and $R^3$ are D-D-serine residues, the compound of Formula I is a tripeptide.

In certain embodiments of Formula I, one of $Y^{2a}$ and $Y^{2b}$ is H and the other is D.

In another aspect, the invention provides a pharmaceutical composition comprising a compound of Formula I:

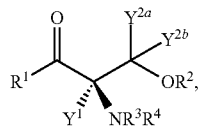
(I)

wherein
$R^1$ is —OH, —OD, —O—$C_{1-4}$ alkyl, or an amino acid residue;
$R^2$ is H, D, —$C_{1-4}$ alkyl, —C(O)—$C_{1-6}$ alkyl, or —C(O)—$C_{1-6}$ hydroxyalkyl;
$R^3$ is H, D, or an amino acid residue;
$R^4$ is H or D;
each of $Y^1$, $Y^{2a}$ and $Y^{2b}$ is independently H or D, provided that at least one of $Y^1$, $Y^{2a}$ and $Y^{2b}$ is D; wherein each position designated specifically as deuterium has at least 50.1% incorporation of deuterium;
or a pharmaceutically acceptable salt thereof;
and a pharmaceutically acceptable carrier.

In certain embodiments, each position designated specifically as deuterium has at least 90% incorporation of deuterium.

In certain embodiments, in the compound of Formula I, $R^1$ or $R^3$ is a D-D-serine residue (a residue of deuterated D-serine).

In certain embodiments of the compositions of the invention, the compound is a compound of Formula II:

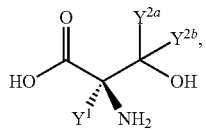
(II)

wherein each of $Y^1$, $Y^{2a}$ and $Y^{2b}$ is independently H or D, provided that at least one of $Y^1$, $Y^{2a}$ and $Y^{2b}$ is D;
or a pharmaceutically acceptable salt thereof.

In certain embodiments, in the compound of Formula II, $Y^1$ is D.

In certain embodiments, in the compound of Formula II, $Y^{2a}$ and $Y^{2b}$ are each H.

In certain embodiments, in the compound of Formula II, $Y^1$ is D, and $Y^{2a}$ and $Y^{2b}$ are each H.

In certain embodiments, in the compound of Formula II, $Y^{2a}$ and $Y^{2b}$ are each D. In other embodiments of Formula II, one of $Y^{2a}$ and $Y^{2b}$ is H and the other is D.

In certain embodiments, the compound of Formula II is selected from Compound 100 and Compound 103:

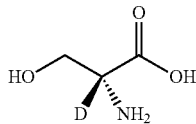
Compound 100

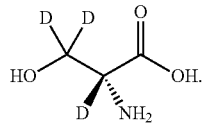
Compound 103

In certain embodiments, in the compound of Formula II, each position designated specifically as deuterium has at least 90% incorporation of deuterium. In certain embodiments, in the compound of Formula II, each position designated specifically as deuterium has at least 95% incorporation of deuterium. In certain embodiments, in the compound of Formula II, each position designated specifically as deuterium has at least 97% incorporation of deuterium.

In certain embodiments, in the compound of Formula II, $Y^1$ is D, and $Y^{2a}$ and $Y^{2b}$ are each H, and $Y^1$ has at least 90% incorporation of deuterium, or at least 95% incorporation of deuterium, or at least 97% incorporation of deuterium.

In certain embodiments, in the compound of Formula II, any atom not designated as deuterium is present at its natural isotopic abundance.

In one aspect, the invention provides a compound of Formula Ia:

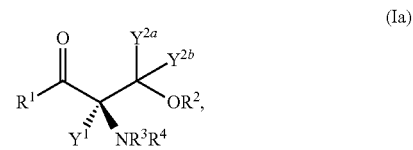
(Ia)

wherein
$R^1$ is —OH,-OD, or —O—$PG^1$, —O—$C_{1-6}$ cycloalkyl or an amino acid residue;
$R^2$ is H, D, —$C_{1-4}$ alkyl, —C(O)—$C_{1-6}$ alkyl, or —C(O)—$C_{1-6}$ hydroxyalkyl; and either
a) $R^3$ is H, D, or $PG^2$; and
 $R^4$ is H or D; wherein each position designated specifically as deuterium has at least 50.1% incorporation of deuterium;
or
b) $R^3$ and $R^4$ together with the nitrogen atom form a heterocyclic protecting group;
wherein $PG^1$ and $PG^2$ are prodrug groups;
or a pharmaceutically acceptable salt thereof.

In certain embodiments, each position designated specifically as deuterium has at least 90% incorporation of deuterium. In certain embodiments, each position designated specifically as deuterium has at least 95% incorporation of deuterium. In certain embodiments, each position designated specifically as deuterium has at least 97% incorporation of deuterium.

The term "prodrug group", as used herein, refers to a group which can be cleaved under physiological conditions (e.g., in vivo) to provide an unprotected moiety (e.g., a carboxylate or an amino group). Thus, PG' can be any group that is cleaved under physiological conditions to provide an unprotected carboxylate group (i.e., a compound of Formula Ia wherein $R^1$ is OH); examples of suitable PG' groups include —$C_{1-6}$ alkyl (such as methyl, ethyl, isopropyl, tert-butyl, neopentyl), —$C_{3-6}$ cycloalkyl (including cyclohexyl), or an amino acid residue. $PG^2$ can be any group that is cleaved under physiological conditions to provide an unprotected amino group; examples of suitable PG² groups include an amino acid residue or a group of the formula: —C(O)OC(Z¹Z²)OR⁵, in which Z¹ and Z² are independently selected from H, D, $C_1$-$C_2$ alkyl, or together form a $C_3$-$C_5$ carbocyle with the carbon atom to which they are attached; and R⁵ is $C_{1-6}$ aliphatic group (including a $C_{1-6}$ alkyl or a partially or entirely unsaturated $C_{2-6}$ aliphatic group), $C_{3-6}$ cycloalkyl, or $C_{4-6}$ carbocyclyl (which can be partially or entirely unsaturated); wherein each R⁵ is optionally further substituted with aryl or heterocycloalkyl. The heterocyclic protecting group formed with R³ and R⁴ can be a group having the structure:

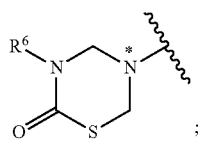

and

R⁶ is methyl, ethyl, n-propyl, n-butyl, cyclohexyl, —CH₂C₆H₅ or —CH₂CH₂C₆H₅.

In certain embodiments, in the compound of Formula Ia, R¹ or R³ is a D-D-serine residue (a residue of deuterated D-serine).

In certain embodiments, the compound of Formula I or II is at least about 90% stereomerically pure, e.g., for a compound of Formula I, the compound comprises at least 90% of the structure

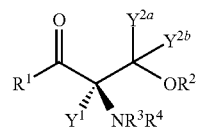

and not more than 10% of

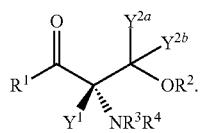

In certain embodiments, the compound of Formula Ia is at least about 90% stereomerically pure, e.g., for a compound of Formula Ia, the compound comprises at least 90% of the structure.

A compound of Formula I or II may exist as a zwitterion (e.g., a compound of Formula II can be represented by the structure:

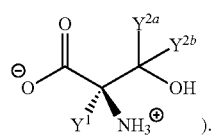

It will be understood that such zwitterionic forms are included within the scope of this invention.

In certain embodiments, the pharmaceutical composition is suitable for oral administration. In certain embodiments, the pharmaceutical composition is suitable for intravenous administration.

In one aspect, the invention provides a pharmaceutical composition comprising a compound of Formula A:

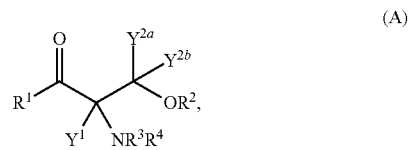

wherein
R¹ is —OH,-OD, —O—$C_{1-4}$ alkyl, or an amino acid residue;
R² is H, D, —$C_{1-4}$ alkyl, —C(O)—$C_{1-6}$ alkyl, or —C(O)—$C_{1-6}$ hydroxyalkyl;
R³ is H, D, or an amino acid residue;
R⁴ is H or D;
each of Y¹, $Y^{2a}$ and $Y^{2b}$ is independently H or D, provided that at least one of Y¹, $Y^{2a}$ and $Y^{2b}$ is D; wherein each position designated specifically as deuterium has at least 50.1% incorporation of deuterium;
or a pharmaceutically acceptable salt thereof;
and a pharmaceutically acceptable carrier;
wherein the composition comprises a therapeutically effective amount of the compound having the D-amino acid configuration.

In certain embodiments, each position designated specifically as deuterium has at least 90% incorporation of deuterium. In certain embodiments, each position designated specifically as deuterium has at least 90% incorporation of deuterium. In certain embodiments, each position designated specifically as deuterium has at least 95% incorporation of deuterium.

When R¹ or R³ is an amino acid residue, the compound of Formula I is a dipeptide where one or both amino acids are D-D-serine.

In certain aspects, this invention relates to deuterated forms of glycine, pharmaceutically acceptable salts thereof, analogs and prodrugs thereof, pharmaceutical compositions thereof, and methods of use thereof.

In certain aspects, the invention provides a pharmaceutical composition comprising a compound of Formula III:

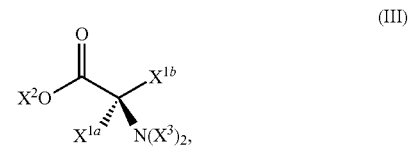

wherein
each of $X^{1a}$, $X^{1b}$, and X² is independently H or D; and
each X³ is H or D;
provided that at least one of $X^{1a}$ and $x^{1b}$ is D;
or a pharmaceutically acceptable salt thereof;
and a pharmaceutically acceptable carrier.

In certain embodiments, in the compound of Formula III, $X^{1a}$ is D, and $X^{1b}$ is H.

In certain embodiments, in the compound of Formula III, $X^{1a}$ is H, and $X^{1b}$ is D.

In certain embodiments, in the compound of Formula III, $X^{1a}$ and $X^{1b}$ are each D.

In some embodiments, the compound is selected from any one of the compounds set forth in Table C (below):

TABLE C

Examples of Compounds of Formula III

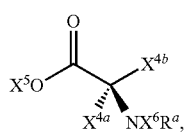

(III)

| Compound # | $X^{1a}$ | $X^{1b}$ | $X^2$ | Each $X^3$ |
|---|---|---|---|---|
| 300 | D | H | H | H |
| 301 | H | D | H | H |
| 302 | D | D | H | H |
| 303 | D | H | D | D |
| 304 | H | D | D | D |
| 305 | D | D | D | D | or a pharmaceutically acceptable salt thereof.

In certain aspects, this invention relates to deuterated forms of sarcosine, pharmaceutically acceptable salts thereof, analogs and prodrugs thereof, pharmaceutical compositions thereof, and methods of use.

In certain aspects, the invention provides a pharmaceutical composition comprising a compound of Formula IV:

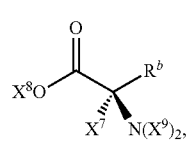

(IV)

wherein
each of $X^{4a}$, $X^{4b}$, $X^5$ and $X^6$ is independently H or D; and
each $R^a$ is $CH_3$, $CH_2D$, $CD_2H$ or $CD_3$;
provided that at least one of $X'$, $X^{4b}$ and $R^a$ comprises D;
or a pharmaceutically acceptable salt thereof;
and a pharmaceutically acceptable carrier.

In certain embodiments, in the compound of Formula IV, $X^{4a}$ is D, and $X^{4b}$ is H.

In certain embodiments, in the compound of Formula IV, $X^{4a}$ is H, and $X^{4b}$ is D.

In certain embodiments, in the compound of Formula IV, $X^{4a}$ and $X^{4b}$ are each D.

In certain embodiments, in the compound of Formula IV, $R^a$ is $CD_3$.

In some embodiments, the compound is selected from any one of the compounds set forth in Table D (below):

TABLE D

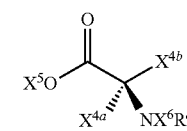

Examples of Compounds of Formula IV (IV)

| Compound # | $X^{4a}$ | $X^{4b}$ | $X^5$ | $X^6$ | $R^a$ |
|---|---|---|---|---|---|
| 400 | D | H | H | H | $CH_3$ |
| 401 | H | D | H | H | $CH_3$ |
| 402 | D | D | H | H | $CH_3$ |
| 403 | D | H | H | H | $CD_3$ |
| 404 | H | D | H | H | $CD_3$ |
| 405 | D | D | H | H | $CD_3$ |
| 406 | D | H | D | D | $CH_3$ |
| 407 | H | D | D | D | $CH_3$ |
| 408 | D | D | D | D | $CH_3$ |
| 409 | D | H | D | D | $CD_3$ |
| 410 | H | D | D | D | $CD_3$ |
| 411 | D | D | D | D | $CD_3$ |
| 412 | H | H | H | H | $CD_3$ |
| 413 | H | H | D | D | $CD_3$ | or a pharmaceutically acceptable salt thereof.

In certain aspects, this invention relates to deuterated forms of D-alanine, pharmaceutically acceptable salts thereof, analogs and prodrugs thereof, pharmaceutical compositions thereof, and methods of use.

In certain aspects, the invention provides a pharmaceutical composition comprising a compound of Formula V:

(V)

wherein
each of $X^7$ and $X^8$ is independently H or D;
each $X^9$ is H or D; and
each $R^b$ is $CH_3$, $CH_2D$, $CD_2H$ or $CD_3$;
provided that at least one of $X^7$ and $R^b$ comprises D;
or a pharmaceutically acceptable salt thereof;
and a pharmaceutically acceptable carrier.

In certain embodiments, in the compound of Formula V, $X^7$ is H and $R^b$ is $CD_3$.

In certain embodiments, in the compound of Formula V, $X^7$ is D and $R^b$ is $CD_3$.

In certain embodiments, in the compound of Formula V, $X^7$ is D and $R^b$ is $CH_3$.

In some embodiments, the compound is selected from any one of the compounds set forth in Table E (below):

TABLE E

Examples of Compounds of Formula V

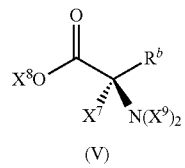

(V)

| Compound # | $X^7$ | $X^8$ | Each $X^9$ | $R^b$ |
|---|---|---|---|---|
| 500 | D | H | H | $CH_3$ |
| 501 | D | D | D | $CH_3$ |
| 502 | D | H | H | $CD_3$ |
| 503 | D | D | D | $CD_3$ |
| 504 | H | H | H | $CD_3$ |
| 505 | H | D | D | $CD_3$ | or a pharmaceutically acceptable salt thereof.

In certain aspects, this invention relates to deuterated forms of D-aspartic acid, pharmaceutically acceptable salts thereof, analogs and prodrugs thereof, pharmaceutical compositions thereof, and methods of use.

In certain aspects, the invention provides a pharmaceutical composition comprising a compound of Formula VI:

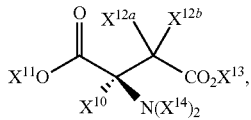

(VI)

wherein each of $X^{10}$, $X^{11}$, $X^{12a}$, $X^{12b}$, and $X^{13}$ is independently H or D; and each $X^{11}$ is H or D;

provided that at least one of $X^{10}$, $X^{12a}$ and $X^{12b}$ is D;

or a pharmaceutically acceptable salt thereof;

and a pharmaceutically acceptable carrier.

In certain embodiments, in the compound of Formula VI, $X^{10}$ is H, $X^{12a}$ is H and $X^{12b}$ is D.

In certain embodiments, in the compound of Formula VI, $X^{10}$ is H, $X^{12a}$ is D and $X^{12b}$ is D.

In certain embodiments, in the compound of Formula VI, $X^{10}$ is D, $X^{12a}$ is H and $X^{12b}$ is H.

In certain embodiments, in the compound of Formula VI, $X^{10}$ is D, $X^{12a}$ is H and $X^{12b}$ is D.

In certain embodiments, in the compound of Formula VI, $X^{10}$ is D, $X^{12a}$ is D and $X^{12b}$ is D.

In some embodiments, the compound is selected from any one of the compounds set forth in Table F (below):

TABLE F

Examples of Compounds of Formula VI

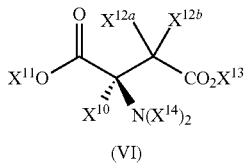

(VI)

| Compound # | $X^{10}$ | $X^{11}$ | $X^{12a}$ | $X^{12b}$ | $X^{13}$ | Each $X^{14}$ |
|---|---|---|---|---|---|---|
| 600 | D | H | H | H | H | H |
| 601 | D | H | D | H | H | H |
| 602 | D | H | D | D | H | H |
| 603 | H | H | D | H | H | H |
| 604 | H | H | D | D | H | H |
| 605 | D | D | H | H | D | D |
| 606 | D | D | D | H | D | D |
| 607 | D | D | D | D | D | D |
| 608 | H | D | D | H | D | D |
| 609 | H | D | D | D | D | D | or a pharmaceutically acceptable salt thereof.

In some embodiments, the compound is selected from any one of the Compounds set forth in Table C, Table D, Table E or Table F (above), or a pharmaceutically acceptable salt thereof; wherein any atom not designated as deuterium is present at its natural isotopic abundance.

In certain embodiments, in the compound of Formula III, IV, V or VI, each position designated specifically as deuterium has at least 90% incorporation of deuterium.

In certain embodiments, in the compound of Formula III, IV, V or VI, any atom not designated as deuterium is present at its natural isotopic abundance.

In certain embodiments, the compound of Formula V or VI is at least about 90% stereomerically pure.

In certain embodiments, the pharmaceutical composition comprising one or more compounds of Formula III, IV, V and VI is suitable for oral administration. In certain embodiments, the pharmaceutical composition comprises 0.1 g to 60 g of the compound of Formula III, IV, V or VI.

In certain embodiments, the pharmaceutical composition comprising one or more compounds of Formula III, IV, V and VI is suitable for intravenous administration. In certain embodiments, the pharmaceutical composition comprises 0.1 g to 60 g of the compound of Formula III, IV, V or VI.

Another aspect of the invention is a unit dose form comprising a compound of Formula I or Formula II, or a pharmaceutically acceptable salt thereof, together with a pharmaceutically acceptable carrier or diluent. In certain embodiments, the amount of a compound of Formula I or Formula II, or a pharmaceutically acceptable salt thereof, is in the range of 1 g to 10 g, or 1 g to 5 g. In certain embodiments, the amount of a compound of Formula I or Formula II, or a pharmaceutically acceptable salt thereof, is about 1 g, about 2 g, about 3 g, about 4 g, or about 5 g, about 8 g, about 10 g, or in the range of about 5 g to about 10 g. In certain embodiments, the amount of a compound of Formula I or Formula II, or a pharmaceutically acceptable salt thereof, is 1 g, 2 g, 3 g, 4 g, 5 g, 8 g, 10 g, or in the range of 5 to 10 g. In certain embodiments, the unit dose form is a tablet. In certain embodiments, the unit dose form is a sachet.

Another aspect of the invention is a packaged pharmaceutical formulation comprising a compound of Formula I or Formula II, or a pharmaceutically acceptable salt thereof, together with a container or package In certain embodiments, the amount of a compound of Formula I or Formula II, or a pharmaceutically acceptable salt thereof, is in the range of 1 g to 10 g, or 1 g to 5 g. In certain embodiments, the amount of a compound of Formula I or Formula II, or a pharmaceutically acceptable salt thereof, is about 1 g, about 2 g, about 3 g, about 4 g, or about 5 g, about 8 g, about 10 g, or in the range of about 5 g to about 10 g. In certain embodiments, the amount of a compound of Formula I or Formula II, or a pharmaceutically acceptable salt thereof, is 1 g, 2 g, 3 g, 4 g, 5 g, 8 g, 10 g, or in the range of 5 to 10 g. In certain embodiments, the packaged pharmaceutical formulation comprises a tablet. In certain embodiments, the packaged pharmaceutical formulation comprises a sachet.

In another aspect, the invention provides therapeutic methods.

In one embodiment, the invention provides a method of treating NMDAR encephalitis, the method comprising administering to a subject in need thereof an effective amount of a pharmaceutical composition of this invention.

In another embodiment, the invention provides a method of treating epilepsy, NMDAR encephalitis, Parkinson's disease, cognitive deficits in Parkinson's disease, Alzheimer's disease, mild cognitive impairment, amyotrophic lateral sclerosis (ALS), Huntington's disease, schizophrenia (including positive, cognitive, and/or negative symptoms of schizophrenia, as well as prodromal schizophrenia), bipolar disorder, bipolar mania, bipolar depression, treatment-refractory depression, cognitive deficits in depression, major depressive disorder, generalized anxiety disorder, major depressive disorder with mixed features, and cognition deficits in associated with diseases or conditions such as Huntington's disease, subjective cognitive decline, traumatic brain injury, Lewy Body Dementia, the method comprising administering to a subject in need thereof an effective amount of a pharmaceutical composition of this invention.

In another embodiment, the invention provides a method of treating Additional diseases or conditions include post-traumatic stress disorder (PTSD), ataxia, and serine deficiency disorders, the method comprising administering to a subject in need thereof an effective amount of a pharmaceutical composition of this invention.

In another embodiment, the invention provides a method of treating depression, the method comprising administering to a subject in need thereof an effective amount of a pharmaceutical composition of this invention.

In another aspect, the invention provides a method of increasing NMDA receptor function, the method comprising contacting a cell with a pharmaceutical composition of this invention, such that NMDA receptor function in the cell is increased.

In another aspect, the invention provides a method of treating schizophrenia (including positive, negative, and/or cognitive symptoms of schizophrenia), the method comprising administering to a subject in need thereof an effective amount of a compound or pharmaceutical composition of the present invention.

In certain embodiments of any of the foregoing compounds, compositions or methods, administration of a compound of this invention (e.g., Compound 100) results in reduced nephrotoxicity compared to administration of an equivalent dose of (non-deuterated) D-Serine.

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

As used herein, the term "subject" includes humans and non-human mammals. Non-limiting examples of non-human mammals include mice, rats, guinea pigs, rabbits, dogs, cats, monkeys, apes, pigs, cows, sheep, horses, etc. In certain embodiments, the subject is a human suffering from schizophrenia.

The term "alkyl" refers to a monovalent saturated hydrocarbon group. A $C_1$-$C_4$ alkyl is an alkyl having from 1 to 4 carbon atoms; a $C_1$-$C_6$ alkyl is an alkyl having from 1 to 6 carbon atoms. In some embodiments, an alkyl may be linear or branched. In some embodiments, an alkyl may be primary, secondary, or tertiary. Non-limiting examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl. Non-limiting examples of primary alkyl groups include methyl, ethyl, n-propyl, n-butyl, n-pentyl, and n-hexyl. Non-limiting examples of secondary alkyl groups include isopropyl, sec-butyl, and 2-methylpentyl. Non-limiting examples of tertiary alkyl groups include t-butyl. A "$C_1$-$C_6$ hydroxyalkyl" group is a $C_1$-$C_6$ alkyl group substituted with one to three hydroxyl groups.

It will be recognized that some variation of natural isotopic abundance occurs in a synthesized compound depending upon the origin of chemical materials used in the synthesis. Thus, a preparation of Compound 1 will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

The term "D-D-serine" refers to a deuterated analog of the amino acid serine in the (D)-configuration. D-D-serine can be represented by the structure of Formula II:

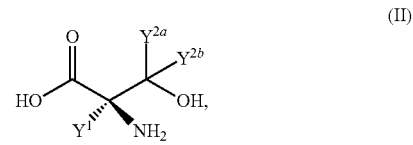

wherein each of $Y^1$, $Y^{2a}$ and $Y^{2b}$ is independently H or D, provided that at least one of $Y^1$, $Y^{2a}$ and $Y^{2b}$ is D.

The term "amino acid residue" refers to a group of the general formula —C(O)—CHR—NH$_2$ or HO—C(O)—CHR—NH—, and N-alkylated derivatives thereof (—C(O)—CHR—N(alkyl)-), wherein R is an amino acid side chain, and includes naturally occurring and synthetic amino acids in a (D)-, (L)- or racemic (D,L) configuration. It will be understood that when the variable $R^1$ or $R^2$ of Formula I herein is an amino acid residue, the amino acid residue is linked to the rest of the molecule through an amide bond. Exemplary amino acids include a residue of any naturally-occurring amino acid, including deuterated forms thereof.

For example, an amino acid residue can be a residue of deuterated D-serine (D-D-serine).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. However, in certain embodiments, where specifically stated, when a position is designated specifically as "H" or "hydrogen", the position has at least 80%, at least 90%, at least 95%, at least 96%, at least 97%, at least 98%, or at least 99% hydrogen. In some embodiments, where specifically stated, when a position is designated specifically as "H" or "hydrogen", the position incorporates ≤20% deuterium, ≤10% deuterium, ≤5% deuterium, ≤4% deuterium, ≤3% deuterium, ≤2% deuterium, or ≤1% deuterium. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, in a compound of this invention, each designated deuterium atom has deuterium incorporation of at least 52.5%. In some embodiments, in a compound of this invention, each designated deuterium atom has deuterium incorporation of at least 60%. In some embodiments, in a compound of this invention, each designated deuterium atom has deuterium incorporation of at least 67.5%. In some embodiments, in a compound of this invention, each designated deuterium atom has deuterium incorporation of at least 75%. In some embodiments, in a compound of this invention, each designated deuterium atom has deuterium incorporation of at least 82.5%. In some embodiments, in a compound of this invention, each designated deuterium atom has deuterium incorporation of at least 90%. In some embodiments, in a compound of this invention, each designated deuterium atom has deuterium incorporation of at least 95%. In some embodiments, in a compound of this invention, each designated deuterium atom has deuterium incorporation of at least 97.5%. In some embodiments, in a compound of this invention, each designated deuterium atom has deuterium incorporation of at least 99%. In some embodiments, in a compound of this invention, each designated deuterium atom has deuterium incorporation of at least 99.5%.

Deuterium incorporation in a compound of the invention can be measured using a variety of techniques, some of which are known in the art. For example, $^1$H NMR can be used to measure deuterium incorporation (e.g., by measuring the absence of or decrease in proton signals corresponding to deuterated positions, e.g., relative to a non-deuterated position or positions).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure will contain molecules having deuterium at each of the positions designated as deuterium in the chemical structure, and may also contain isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound.

The invention also provides salts of the compounds of the invention.

A salt of a compound of this invention is formed between an acid and a basic group of the compound, such as an amino functional group, or a base and an acidic group of the compound, such as a carboxyl functional group. According to one embodiment, the compound is a pharmaceutically acceptable acid addition salt. In one embodiment the acid addition salt may be a deuterated acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid. In one embodiment, the acids commonly employed to form pharmaceutically acceptable salts include the above-listed inorganic acids, wherein at least one hydrogen is replaced with deuterium.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Certain compounds of the present invention (e.g., compounds of Formula I, II, V or VI) contain an asymmetric carbon atom (i.e., the carbon bearing the —$NH_2$ or $NR^3R^4$ and $Y^1$ groups in a compound of Formula I or II) and may contain one or more additional asymmetric carbon atoms. In certain embodiments, a compound of Formula I or II is a deuterated D-serine analog substantially free from other possible stereoisomers, e.g., a compound of Formula I is substantially free of a compound of the structure:

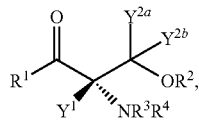

and a compound of Formula II is substantially free of a compound of the structure:

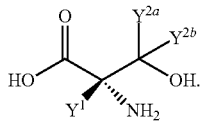

The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual stereoisomer (e.g., enantiomer or diastereomer) for a given compound are known in the art and may be applied as practicable to final compounds or to starting material or intermediates.

Unless otherwise indicated, when a disclosed compound is named or depicted by a structure having one or more chiral centers of unspecified stereochemistry, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers. "Tert" and "t-" each refer to tertiary. "Sec" or "s-" each refer to secondary. "n-" refers to normal. "i-" refers to iso. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

As used herein, the term "schizophrenia" refers to a psychiatric disorder that includes at least two of the following: delusions, hallucinations, disorganized speech, grossly disorganized or catatonic behavior, or negative symptoms. Patients may be diagnosed as schizophrenic using the DSM-IV criteria (APA, 2013, Diagnostic and Statistical Manual of Mental Disorders (Fifth Edition), Washington, D.C.).

"Negative" symptoms of schizophrenia include affect blunting, anergia, alogia and social withdrawal, which can be measured using SANS (the Scales for the Assessment of Negative Symptoms; see Andreasen, 1983, Scales for the Assessment of Negative Symptoms (SANS), Iowa City, Iowa).

"Positive" symptoms of schizophrenia include delusion and hallucination, which can be measured using PANSS (the Positive and Negative Syndrome Scale; see Kay et al., 1987, Schizophrenia Bulletin 13:261-276).

"Cognitive" symptoms of schizophrenia include impairment in obtaining, organizing, and using intellectual knowledge which can be measured by the Positive and Negative Syndrome Scale-cognitive subscale (PANSS-cognitive subscale) (Lindenmayer et al., 1994, J. Nerv. Ment. Dis. 182: 631-638) or with cognitive tasks such as the Wisconsin Card Sorting Test.

Therapeutic Compositions

In certain aspects or embodiments, the present invention provides a pharmaceutical composition comprising a compound of Formula I:

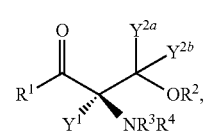

wherein
$R^1$ is —OH, -OD, —O—$C_{1-4}$ alkyl, or an amino acid residue;
$R^2$ is H, D, —$C_{1-4}$ alkyl, —C(O)—$C_{1-6}$ alkyl, or —C(O)—$C_{1-6}$ hydroxyalkyl;
$R^3$ is H, D, or an amino acid residue;
$R^4$ is H or D; and
each of $Y^1$, $Y^{2a}$ and $Y^{2b}$ is independently H or D, provided that at least one of $Y^1$, $Y^{2a}$ and $Y^{2b}$ is D;
or a pharmaceutically acceptable salt thereof;
and a pharmaceutically acceptable carrier.

In certain embodiments of the compound of Formula I, $R^1$ or $R^3$ is a D-D-serine residue (the compound is a dipeptide).

In another aspect, the invention provides a pharmaceutical composition comprising a compound of Formula Ia, or a pharmaceutically acceptable salt thereof, and a pharmaceutically acceptable carrier.

In certain embodiments, the compound is a compound of Formula II:

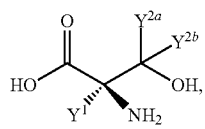

(II)

wherein each of $Y^1$, $Y^{2a}$ and $Y^{2b}$ is independently H or D, provided that at least one of $Y^1$, $Y^{2a}$ and $Y^{2b}$ is D; or a pharmaceutically acceptable salt thereof.

In certain embodiments of the compound of Formula I or Formula II, $Y^1$ is D.

In certain embodiments of the compound of Formula I or Formula II, $Y^{2a}$ and $Y^{2b}$ are each H.

In certain embodiments of the compound of Formula I or Formula II, $Y^{2a}$ and $Y^{2b}$ are each D.

In certain embodiments, the compound of Formula II is selected from Compound 100 and Compound 103:

Compound 100

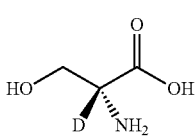

Compound 103

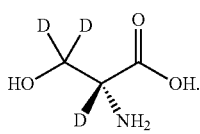

In certain embodiments of the compound of Formula I or Formula II, each position designated specifically as deuterium has at least 90% incorporation of deuterium.

In certain embodiments, in the compound of Formula II, $Y^1$ is D, and $Y^{2a}$ and $Y^{2b}$ are each H, and $Y^1$ has at least 90% incorporation of deuterium, or at least 95% incorporation of deuterium, or at least 97% incorporation of deuterium.

In certain embodiments of the compound of Formula I or Formula II, any atom not designated as deuterium is present at its natural isotopic abundance.

In certain embodiments of the compound of Formula I or Formula II, the compound is at least about 90% stereomerically pure.

In some embodiments, the compound is selected from any one of the compounds set forth in Table A (below):

TABLE A

Examples of Compounds of Formula II

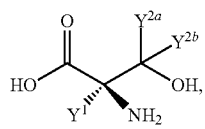

(II)

| Compound # | $Y^1$ | $Y^{2a}$ | $Y^{2b}$ | $R^1$ |
|---|---|---|---|---|
| 100 | D | H | H | OH |
| 101 | D | D | H | OH |
| 102 | D | H | D | OH |
| 103 | D | D | D | OH |
| 104 | H | D | D | OH |
| 105 | H | D | H | OH |
| 106 | H | H | D | OH | or a pharmaceutically acceptable salt thereof.

In a specific embodiment, the compound is Compound 100:

Compound 100

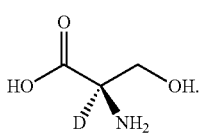

In another specific embodiment, the compound is Compound 103:

Compound 103

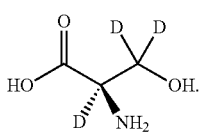

In some embodiments, the compound is selected from any one of the compounds (Cmpd) set forth in Table B (below):

TABLE B

Examples of Compounds of Formula I

![Formula I structure: R¹-C(=O)-C(Y¹)(NR³R⁴)-C(Y²ᵃ)(Y²ᵇ)-OR²]

(I)

| Compound | $Y^1$ | $Y^{2a}$ | $Y^{2b}$ | $R^1$ | $R^2$ | $R^3$ | $R^4$ |
|---|---|---|---|---|---|---|---|
| 200 | D | H | H | [serine-D acyl group: HO-C(=O)-C(D)(NH—)-CH₂OH] | H | [serine-D acyl group: C(=O)-C(D)(NH₂)-CH₂OH] | H |
| 201 | D | H | H | [serine-D acyl group: HO-C(=O)-C(D)(NH—)-CH₂OH] | H | H | H |
| 202 | D | H | H | H | L-lactate | H | H |
| 203 | D | H | H | —O-ethyl | H | H | H |
| 204 | D | H | H | [serine-D,D,D acyl group: HO-C(=O)-C(D)(NH—)-CD₂OH] | H | [serine-D acyl group: C(=O)-C(D)(NH₂)-CH₂OH] | H |
| 205 | D | H | H | [serine-D,D,D acyl group: HO-C(=O)-C(D)(NH—)-CD₂OH] | H | H | H | or a pharmaceutically acceptable salt thereof.

In some embodiments, the compound is selected from any one of the Compounds set forth in Table A or Table B (above), or a pharmaceutically acceptable salt thereof; wherein any atom not designated as deuterium is present at its natural isotopic abundance.

In some embodiments of a compound of this invention, when $Y^1$ is deuterium, the level of deuterium incorporation at $Y^1$ is at least 52.5%, at least 75%, at least 82.5%, at least 90%, at least 95%, at least 97%, or at least 99%.

In some embodiments of a compound of this invention, when $Y^{2a}$ or $Y^{2b}$ is deuterium, the level of deuterium incorporation at each $Y^{2a}$ or $Y^{2b}$ designated as deuterium is at least 52.5%, at least 75%, at least 82.5%, at least 90%, at least 95%, at least 97%, or at least 99%.

In another set of embodiments, any atom not designated as deuterium in any of the embodiments set forth herein is present at its natural isotopic abundance.

In some embodiments of a compound of this invention, deuterium incorporation at each designated deuterium atom is at least 52.5%, at least 75%, at least 82.5%, at least 90%, at least 95%, at least 97%, or at least 99%.

In some embodiments of a compound of this invention, at least one of $Y^1$, $Y^{2a}$, and $Y^{2b}$, is hydrogen.

The present invention also provides deuterated intermediates useful, e.g., in the preparation of the compounds of Formula I, and as provided in the Exemplary Schemes.

The synthesis of compounds of Formula I may be readily achieved by synthetic chemists of ordinary skill by reference to the Exemplary Synthesis and Examples disclosed herein. Relevant procedures analogous to those of use for the preparation of compounds of Formula I and intermediates thereof are disclosed, for instance in U.S. Pat. No. 4,582,931.

The synthesis of compounds of Formula III, IV, V and VI may be readily achieved by synthetic chemists of ordinary skill by reference to the Exemplary Synthesis and Examples disclosed herein, using appropriate starting materials and reagents.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I or II is depicted in Scheme 1.

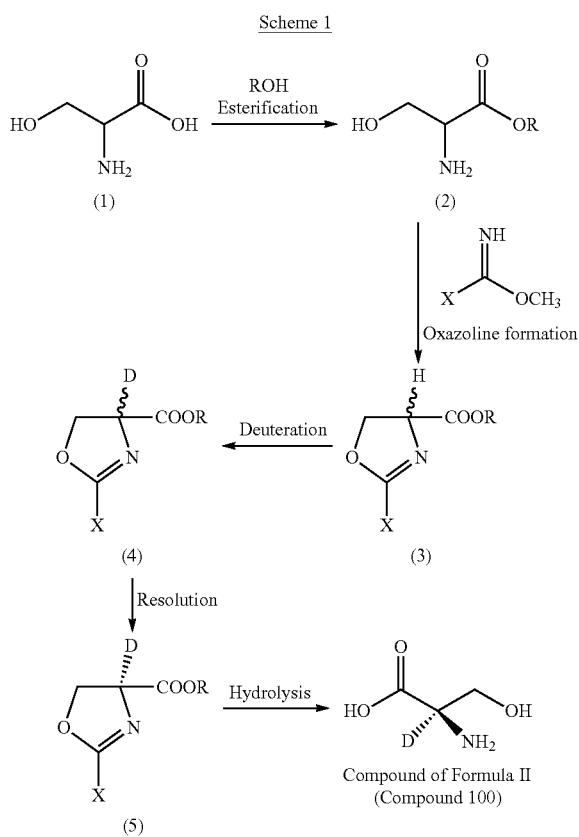

As depicted in Scheme 1, and as described in more detail in U.S. Pat. No. 4,582,931, esterification of dl-serine (1) results in formation of the serine ester (2), which can be cyclized to the oxazoline (3) using benzoimidate. Oxazoline (3) is then deuterated by deprotonation with a strong base (such as butyllithium) and quenching with a deuterium source (such as acetic acid O-D) to produce deuterated intermediate (4), which is resolved (e.g., using a chiral salt such as d-α-bromocamphorsulfonic acid or separating the enantiomers using SMB (simulated moving bed) chromatography) to provide intermediate (5) (as the salt). After neutralizing the salt, the oxazoline (5) is then hydrolyzed to provide a compound of Formula II (Scheme 1 illustrates preparation of Compound 100).

Use of appropriately deuterated reagents allows deuterium incorporation at the $Y^1$, $Y^{2a}$, and $Y^{2b}$ positions of a compound of Formula I or II, e.g., about 90%, about 95%, about 97%, or about 99% deuterium incorporation at $Y^1$, $Y^{2a}$, and $Y^{2b}$. For example, Compound 103 can be prepared by using 2-amino-2,3,3-trideuterio-3-hydroxy-propanoic acid (which is commercially available, e.g., from Sigma-Aldrich) as the starting material in the general procedure of Scheme 1; in this instance, the deuteration step of Scheme 1 is not required and is omitted.

Certain compounds of Formulae III and IV are known and in some cases may be commercially available. Compounds of Formula III and IV may be prepared according to methods known in the art.

Certain compounds of Formulae V and VI are commercially available at high enantiomeric purity, or may be purchased as a mixture of enantiomers and resolved as shown above or by using resolution methods well-known in the art, or may be prepared according to methods known in the art.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I-VI and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, Comprehensive Organic Transformations, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention provides pharmaceutical compositions comprising an effective amount of a compound of Formula I, or II (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

In another aspect, the invention provides a pharmaceutical composition comprising a compound of Formula Ia.

The invention further provides pharmaceutical compositions comprising an effective amount of a compound of Formula III, IV, V or VI (e.g., including any of the formulae herein), or a pharmaceutically acceptable salt of said compound; and a pharmaceutically acceptable carrier.

The invention still further provides pharmaceutical compositions comprising in combination an effective amount of two or more compounds selected from a compound of Formula I, II, III, IV, V and VI (e.g., including any of the formulae herein), or a pharmaceutically acceptable salt of each said compound; and a pharmaceutically acceptable carrier.

The invention still further provides pharmaceutical compositions comprising in combination an effective amount of (i) a compound of Formula I or II, or a pharmaceutically acceptable salt thereof, and (ii) one or more compounds selected from glycine, sarcosine, (nondeuterated) D-alanine and (nondeuterated) D-aspartic acid, or a pharmaceutically acceptable salt thereof; and a pharmaceutically acceptable carrier.

The invention still further provides pharmaceutical compositions comprising in combination an effective amount of two or more compounds selected from a compound of Formula III, IV, V, VI (e.g., including any of the formulae herein) and (nondeuterated) D-serine, or a pharmaceutically acceptable salt of each said compound; and a pharmaceutically acceptable carrier.

The invention still further provides pharmaceutical compositions comprising in combination an effective amount of two or more compounds selected from a compound of Formula III, IV, V, VI (e.g., including any of the formulae herein) and D-serine, or a pharmaceutically acceptable salt of each said compound; and a pharmaceutically acceptable carrier.

In a particular embodiment, the invention provides a pharmaceutical composition comprising in combination an effective amount of a compound of Formula I and sarcosine. In a further embodiment, the invention provides a pharmaceutical composition comprising in combination an effective amount of Compound 100 and sarcosine. In a further embodiment, the invention provides a pharmaceutical composition comprising in combination an effective amount of Compound 103 and sarcosine.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000). A unit dosage form can comprise, e.g., 100 mg to 1 g, or 500 mg to 2 g, of a compound of Formula I or II. A unit dosage form can further include one or more second therapeutic agents, e.g., an antipsychotic agent or other agent for the treatment of schizophrenia. A unit dosage form can be administered once per day, or multiple times per day (e.g., twice per day, three times per day, or four times per day). In certain embodiments, the unit dosage form is administered once per day. In other embodiments, the unit dosage form is administered twice per day. In other embodiments, the unit dosage form is administered three times per day. In other embodiments, the unit dosage form is administered four times per day.

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

In another embodiment, a composition of this invention further comprises one or more additional therapeutic agents. The additional therapeutic agent may be selected from any compound or therapeutic agent known to have or that demonstrates advantageous properties when administered with a compound having the same mechanism of action as D-serine. Such agents include those indicated as being useful in combination with D-serine, including but not limited to, those described in U.S. Pat. Nos. 9,040,581 and 9,687,460.

In certain embodiments, the additional therapeutic agent is an agent useful in the treatment of a disease or condition selected from epilepsy, NMDAR encephalitis, Parkinson's disease, cognitive deficits in Parkinson's disease, Alzheimer's disease, mild cognitive impairment, amyotrophic lateral sclerosis (ALS), Huntington's disease, schizophrenia (including positive, cognitive, and/or negative symptoms of schizophrenia, as well as prodromal schizophrenia), bipolar disorder, bipolar mania, bipolar depression, treatment-refractory depression, cognitive deficits in depression, major depressive disorder, generalized anxiety disorder, major depressive disorder with mixed features, and cognition deficits in associated with diseases or conditions such as Huntington's disease, subjective cognitive decline, traumatic brain injury, Lewy Body Dementia, and the like.

In certain embodiments, a pharmaceutical composition containing a deuterated analog of D-serine (or other compound described herein) can be administered to a patient suffering from schizophrenia along with, or in sequence with, an art-known additional therapeutic agent for treating schizophrenia (e.g., olanzapine, clozapine, haloperidol, and the like). Such pharmaceutical compositions are included within the invention. In general, the antipsychotic therapeutic typically is administered at a dosage of 0.25-5000 mg/day (e.g., 5-1000 mg/day)). "Typical" antipsychotics are conventional antipsychotics such as phenothiazine, butryophenones, thioxantheses, dibenzoxazepines, dihydroindolones, and diphenylbutylpiperidines. "Atypical" antipsychotics are a newer generation of antipsychotics which generally act on the dopamine D2 and 5HT$_2$ serotonin receptor and have high levels of efficacy and a benign extrapyramidal symptom side effect profile. Examples of typical antipsychotics include chlorpromazine, thioridazine, mesoridazine, fluphenazine, perphenazine, trifluoperazine, thiothixene, haloperidol, loxapine, molindone, acetophenazine, chlorprothixene, droperidol, and pimozide. Examples of atypical antipsychotics include bolanserin, clozapine, risperidone, olanzapine, cariprazine, asenapine, lurasidone, brexpiprazole, lumateperone, aripiprazole, aripiprazole lauroxil, iloperidone, paliperidone, ziprasidone, and quetiapine. Depot antipsychotics also can be used, e.g., haloperidol decanoate, fluphenazine decanoate, and fluphenazine enanthate. Additional antipsychotics include butaperazine, carphenazine, remoxipride, piperacetazine, and sulpiride.

In certain embodiments, a pharmaceutical composition containing a deuterated analog of D-serine (or other compound described herein) can be administered to a patient with symptoms of schizophrenia together with, or in sequence with, one or more art-known drugs for treating schizophrenia (including antipsychotic agents, e.g., olanzapine, clozapine, haloperidol, quetiapine, risperidone, chlorpromazine and the like). In a particular embodiment, the pharmaceutical composition is for administration to a patient with a DSM-V diagnosis of schizophrenia for at least one year. In a further embodiment, the pharmaceutical composition is for administration to a patient with a PANSS total score of 70-110. In a further embodiment, the pharmaceutical composition is for administration to a patient meeting the additional PANSS criteria:
  a. PANSS score of ≤5 on positive scale items of conceptual disorganization and hostility
  b. PANSS score≥4 on at least two of the following items:
    i. Delusions
    ii. Hallucinations
    iii. Suspiciousness/Persecution
    iv. Unusual thought content In a further embodiment, the pharmaceutical composition is for administration to a patient with clinically stable disease, defined as no hospitalization and no change in medications, for at least 3 months. In a further embodiment, the patient is currently being treated with a maximum of one primary atypical antipsychotic and one low-dose atypical antipsychotic (such as low-dose Seroquel® for sleep or low-dose mood stabilizer) where the sum of primary and secondary antipsychotics is ≤6 mg of risperidone equivalents or 600 mg of chlorpromazine equivalents, respectively, wherein the dose of the antipsychotic medications remain stable for 4 weeks In general, the antipsychotic therapeutic typically is administered at a dosage of 0.25-5000 mg/d (e.g., 5-1000 mg/d)). "Typical" antipsychotics are conventional antipsychotics such as phenothiazine, butryophenones, thioxantheses, dibenzoxazepines, dihydroindolones, and diphenylbutylpiperidines. "Atypical" antipsychotics are a newer generation of antipsychotics which generally act on the dopamine D2 and 5HT$_2$ serotonin receptor and have high levels of efficacy and a benign extrapyramidal symptom side effect profile. Examples of typical antipsychotics include chlorpromazine, thioridazine, mesoridazine, fluphenazine, perphenazine, trifluoperazine, thiothixene, haloperidol, loxapine, molindone, acetophenazine, chlorprothixene, droperidol, and pimozide. Examples of atypical antipsychotics include bolanserin, clozapine, risperidone, olanzapine, cariprazine, asenapine, lurasidone, brexpiprazole, lumateperone, aripiprazole, aripiprazole lauroxil, iloperidone, paliperidone, ziprasidone, and quetiapine. Depot antipsychotics also can be used, e.g., haloperidol decanoate, fluphenazine decanoate, and fluphenazine enanthate. Additional antipsychotics include butaperazine, carphenazine, remoxipride, piperacetazine, and sulpiride.

In another embodiment, the invention provides separate dosage forms of a compound of this invention and one or more of any of the above-described additional therapeutic agents, wherein the compound and additional therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder. As described above, the dosing regimen can include one or more additional therapeutic agents (e.g., where the compound or composition of the invention is used in a combination (e.g., when a compound or composition of the invention is used as an adjunctive therapy).

The term "subject in need thereof," refers to a subject having or being diagnosed with a disease or condition selected from epilepsy, NMDAR encephalitis, Parkinson's disease, cognitive deficits in Parkinson's disease, Alzheimer's disease, mild cognitive impairment, amyotrophic lateral sclerosis (ALS), Huntington's disease, schizophrenia (including positive, cognitive, and/or negative symptoms of schizophrenia, as well as prodromal schizophrenia), bipolar disorder, bipolar mania, bipolar depression, treatment-refractory depression, cognitive deficits in depression, major depressive disorder, generalized anxiety disorder, major depressive disorder with mixed features, and cognition deficits associated with diseases or conditions such as Huntington's disease, subjective cognitive decline, traumatic brain injury, Lewy Body Dementia, and the like.

The interrelationship of dosages for animals and humans (based on milligrams per meter squared of body surface) is described in, e.g., Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In certain embodiments, the pharmaceutical composition comprises an effective amount of the compound of Formula I or II that is in the range from 0.1 g to 60 g. In certain embodiments, an effective amount of a compound of Formula I or Formula II is in the range from 1 to 60 g/day, or from 5 to 30 g/day, or from 10 to 20 g/day. In certain embodiments, an effective amount of a compound of Formula I or Formula II is in the range from 100 mg to 1 g/day. In certain embodiments, an effective amount of a compound of Formula I or Formula II is in the range from 1 to 10 g/day. In certain embodiments, an effective amount of a compound of Formula I or Formula II is in the range from 1 to 8 g/day.

In certain embodiments, an effective amount of Compound 100 is in the range from 1 g/day to 10 g/day, or in the range from 1 g/day to 5 g/day, or in the range from 2 g/day to 4 g/day. In certain embodiments, the pharmaceutical composition comprises 1 g of Compound 100, 2 g of Compound 100, 3 g of Compound 100, 5 g of Compound 100, 8 g of Compound 100, or 10 g of Compound 100.

In certain embodiments, an effective amount of a compound of Formula I or Formula II is in the range from 30 milligrams per kilogram body weight per day (mg/kg/day) to 900 mg/kg/day, or from 60 mg/kg/day to 300 mg/kg/day, or from 150 mg/kg/day to 300 mg/kg/day. In certain embodiments, an effective amount of a compound of Formula I or Formula II is in the range from 30 mg/kg/day to 120 mg/kg/day. In certain embodiments, an effective amount of a compound of Formula I or Formula II is in the range from 10 mg/kg/day to 150 mg/kg/day, or 10 mg/kg/day to 120 mg/kg/day, or 10 mg/kg/day to 90 mg/kg/day.

In certain embodiments, an effective amount of a compound of Formula III, IV, V or VI is in the range from 1 to 60 g/day, or from 5 to 30 g/day, or from 10 to 20 g/day.

In certain embodiments, an effective amount of a compound of Formula III, IV, V or VI is in the range from 30 mg/kg/day to 900 mg/kg/day, or from 60 mg/kg/day to 300 mg/kg/day, or from 150 mg/kg/day to 300 mg/kg/day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for Compound 1.

For pharmaceutical compositions that comprise one or more additional therapeutic agents, an effective amount of the additional therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these additional therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

Some of the additional therapeutic agents referenced above may act synergistically with the compounds of this invention. When this occurs, it will allow the effective dosage of the additional therapeutic agent and/or the compound of this invention to be reduced from that required in a monotherapy. This has the advantage of minimizing toxic side effects of either the additional therapeutic agent of a compound of this invention, synergistically improving efficacy, improving ease of administration or use and/or reduced overall expense of compound preparation or formulation.

Methods of Treatment

In another aspect, the invention provides a method of modulating the activity of NMDAR in a cell, comprising contacting a cell with one or more compounds of Formula I or II herein, or a pharmaceutically acceptable salt thereof. In some embodiments, the cell is contacted in vitro. In some embodiments, the cell is contacted in vivo. In some embodiments, the cell is contacted ex vivo.

In another aspect, the invention provides a method of treating a disease or condition that is beneficially treated by D-serine in a subject in need thereof, comprising the step of administering to the subject an effective amount of a compound of Formula I or II or a pharmaceutical composition comprising a compound of Formula I or II, such that the disease or condition is treated. In another aspect, the invention provides a method of treating a disease or condition that is beneficially treated by D-serine in a subject in need thereof, comprising the step of administering to the subject an effective amount of a compound of Formula Ia or a pharmaceutical composition comprising a compound of Formula Ia, such that the disease or condition is treated.

Such diseases include, but are not limited to, epilepsy, NMDAR encephalitis, Parkinson's disease, cognitive deficits in Parkinson's disease, Alzheimer's disease, mild cognitive impairment, amyotrophic lateral sclerosis (ALS), Huntington's disease, schizophrenia (including positive, cognitive, and/or negative symptoms of schizophrenia, as well as prodromal schizophrenia), bipolar disorder, bipolar mania, bipolar depression, treatment-refractory depression, cognitive deficits in depression, major depressive disorder, generalized anxiety disorder, major depressive disorder with mixed features, and cognition deficits in associated with diseases or conditions such as Huntington's disease, subjective cognitive decline, traumatic brain injury, Lewy Body Dementia, and the like. Additional diseases or conditions include post-traumatic stress disorder (PTSD), ataxia, and serine deficiency disorders.

In certain embodiments, the method of this invention is used to treat a disease or condition selected from epilepsy and NMDAR encephalitis in a subject in need thereof. The method comprises administering to the subject in need thereof an effective amount of a compound of Formula I or II or a pharmaceutical composition comprising a compound of Formula I or II, such that the disease or condition is treated.

This invention also provides a method of treating schizophrenia (including positive, negative, and/or cognitive symptoms of schizophrenia), the method comprising administering to a subject in need thereof an effective amount of a compound or pharmaceutical composition of the present invention (e.g., a compound of Formula I or II, or a compound of Formula Ia; or a pharmaceutical composition comprising compound of Formula I or II, or a compound of Formula Ia). In certain embodiments, the method further comprises administering an antipsychotic therapeutic agent to the subject. In certain embodiments, the method further comprises administering a second therapeutic agent to the subject, wherein the second agent is an antipsychotic therapeutic agent.

In certain embodiments, negative and/or positive and/or cognitive symptom(s) of schizophrenia can be measured before and after treatment of the subject or patient. A reduction in such a symptom(s) indicates that the patient's condition has improved. Improvement in the symptoms of schizophrenia can be assessed using the Scales for the Assessment of Negative Symptoms (SANS) or Positive and Negative Syndrome Scale (PANSS) (see, e.g., Andreasen, 1983, Scales for the Assessment of Negative Symptoms (SANS), Iowa City, Iowa and Kay et al., 1987, Schizophrenia Bulletin 13:261-276). Likewise, one can measure improvement of other neuropsychiatric disorders in patients who have been treated by the methods of the invention. In certain embodiments, positive symptoms of schizophrenia are improved after treatment, relative to pre-treatment symptoms. In certain embodiments, negative symptoms of schizophrenia are improved after treatment, relative to pre-treatment symptoms. In certain embodiments, cognitive symptoms of schizophrenia are improved after treatment, relative to pre-treatment symptoms.

In certain embodiments, the method of treating schizophrenia includes administering a pharmaceutical composition containing a deuterated analog of D-serine (or other compound described herein) to a patient suffering from schizophrenia along with, or in sequence with, an art-known drug for treating schizophrenia (including antipsychotic agents, e.g., olanzapine, clozapine, haloperidol, and the like). In some embodiments, the patient suffering from schizophrenia is stable on antipsychotic therapy, i.e., an existing antipsychotic therapy, prior to treatment as described herein (e.g., a Compound of Formula I or II is used as adjunctive therapy, in conjunction with an additional antipsychotic therapeutic agent). In general, the antipsychotic therapeutic typically is administered at a dosage of 0.25-5000 mg/d (e.g., 5-1000 mg/d)). "Typical" antipsychotics are conventional antipsychotics such as phenothiazine, butryophenones, thioxantheses, dibenzoxazepines, dihydroindolones, and diphenylbutylpiperidines. "Atypical" antipsychotics are a newer generation of antipsychotics which generally act on the dopamine D2 and $5HT_2$ serotonin receptor and have high levels of efficacy and a benign extrapyramidal symptom side effect profile. Examples of typical antipsychotics include chlorpromazine, thioridazine, mesoridazine, fluphenazine, perphenazine, trifluoperazine, thiothixene, haloperidol, loxapine, molindone, acetophenazine, chlorprothixene, droperidol, and pimozide. Examples of atypical antipsychotics include bolanserin, clozapine, risperidone, olanzapine, cariprazine, asenapine, lurasidone, brexpiprazole, lumateperone, aripiprazole, aripiprazole lauroxil, iloperidone, paliperidone, ziprasidone, and quetiapine. Depot antipsychotics also can be used, e.g., haloperidol decanoate, fluphenazine decanoate, and fluphenazine enanthate. Additional antipsychotics include butaperazine, carphenazine, remoxipride, piperacetazine, and sulpiride.

In certain embodiments, the method of treating schizophrenia includes administering a pharmaceutical composition containing a deuterated analog of D-serine (or other compound described herein) to a patient with symptoms of schizophrenia along with, or in sequence with, one or more art-known drugs for treating schizophrenia (including antipsychotic agents, e.g., olanzapine, clozapine, haloperidol, quetiapine, risperidone, chlorpromazine and the like). In a particular embodiment, the pharmaceutical composition is for administration to a patient with a DSM-V diagnosis of schizophrenia for at least one year. In a further embodiment, the pharmaceutical composition is for administration to a patient with a PANSS total score of 70-110. In a further embodiment, the pharmaceutical composition is for administration to a patient meeting the additional PANSS criteria:
   c. PANSS score of ≤5 on positive scale items of conceptual disorganization and hostility
   d. PANSS score≥4 on at least two of the following items:
     i. Delusions
     ii. Hallucinations
     iii. Suspiciousness/Persecution
     iv. Unusual thought content In a further embodiment, the pharmaceutical composition is for administration to a patient with clinically stable disease, defined as no hospitalization and no change in medications, for at least 3 months. In a further embodiment, the patient is currently being treated with a maximum of one primary atypical antipsychotic and one low-dose atypical antipsychotic (such as low-dose Seroquel® for sleep or low-dose mood stabilizer) where the sum of primary and secondary antipsychotics is ≤6 mg of risperidone equivalents or 600 mg of chlorpromazine equivalents, respectively, wherein the dose of the antipsychotic medications remain stable for 4 weeks In general, the antipsychotic therapeutic typically is administered at a dosage of 0.25-5000 mg/d (e.g., 5-1000 mg/d)). "Typical" antipsychotics are conventional antipsychotics such as phenothiazine, butryophenones, thioxantheses, dibenzoxazepines, dihydroindolones, and diphenylbutylpiperidines. "Atypical" antipsychotics are a newer generation of antipsychotics which generally act on the dopamine $D_2$ and $5HT_2$ serotonin receptor and have high levels of efficacy and a benign extrapyramidal symptom side effect profile. Examples of typical antipsychotics include chlorpromazine, thioridazine, mesoridazine, fluphenazine, perphenazine, trifluoperazine, thiothixene, haloperidol, loxapine, molindone, acetophenazine, chlorprothixene, droperidol, and pimozide. Examples of atypical antipsychotics include bolanserin, clozapine, risperidone, olanzapine, cariprazine, asenapine, lurasidone, brexpiprazole, lumateperone, aripiprazole, aripiprazole lauroxil, iloperidone, paliperidone, ziprasidone, and quetiapine. Depot antipsychotics also can be used, e.g., haloperidol decanoate, fluphenazine decanoate, and fluphenazine enanthate. Additional antipsychotics include butaperazine, carphenazine, remoxipride, piperacetazine, and sulpiride.

In certain embodiments, the degree or extent of nephrotoxicity in the subject is reduced compared to treatment with an equivalent amount of D-serine (e.g., a molar equivalent amount of D-serine). Nephrotoxicity can be monitored by measuring levels of markers such as serum creatinine levels or blood urea nitrogen (BUN). A range of about 7 to 20 mg/dL (2.5 to 7.1 mmol/Z) is considered normal for BUN. A range of approximately 0.6 to 2 milligrams (mg) per deciliter (dL) in adult males and 0.5 to 1.1 milligrams per deciliter in adult females is considered normal for serum creatinine. In certain embodiments, the serum creatinine and/or the BUN level is maintained in a normal range during and after treatment.

In certain embodiments, a method of treating schizophrenia comprises administering to subject in need thereof a pharmaceutical composition comprising a compound of Formula II, or a pharmaceutically acceptable salt thereof, and a pharmaceutically acceptable carrier, wherein the amount of the compound of Formula I or II administered per day is in the range of 10 mg/kg to 120 mg/kg (i.e., 10 mg per kilogram of body weight of the subject to 120 per kilogram of body weight of the subject), and wherein the serum creatinine level or the BUN level (or both) of the subject is maintained in the normal range (as described above).

In certain embodiments, the compound of Formula I or II or a pharmaceutical composition comprising a compound of Formula I or II is administered once per day. In certain embodiments, Compound 100 or a pharmaceutical composition comprising Compound 100 is administered once per day. In other embodiments, the compound of Formula I or II or a pharmaceutical composition comprising a compound of Formula I or II is administered twice per day. In certain embodiments, Compound 100 or a pharmaceutical composition comprising Compound 100 is administered twice per day. In yet other embodiments, the compound of Formula I or II or a pharmaceutical composition comprising a compound of Formula I or II is administered three times per day. In certain embodiments, Compound 100 or a pharmaceutical composition comprising Compound 100 is administered three times per day. In yet other embodiments, the compound of Formula I or II or a pharmaceutical composition comprising a compound of Formula I or II is administered four times per day. In certain embodiments, Compound 100 or a pharmaceutical composition comprising Compound 100 is administered four times per day.

In certain embodiments, an effective amount of a compound of Formula I or Formula II is in the range from 1 to 60 g/day, or from 5 to 30 g/day, or from 10 to 20 g/day. In certain embodiments, an effective amount of a compound of Formula I or Formula II is in the range from 100 mg to 1 g/day. In certain embodiments, an effective amount of a compound of Formula I or Formula II is in the range from 1 to 10 g/day.

In certain embodiments, an effective amount of a compound of Formula I or Formula II is in the range from 30 mg/kg/day to 900 mg/kg/day, or from 60 mg/kg/day to 300 mg/kg/day, or from 150 mg/kg/day to 300 mg/kg/day. In certain embodiments, an effective amount of a compound of Formula I or Formula II is in the range from 10 mg/kg/day to 150 mg/kg/day, or 10 mg/kg/day to 120 mg/kg/day, or 10 mg/kg/day to 90 mg/kg/day.

Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject in need thereof one or more additional therapeutic agents. The choice of additional therapeutic agent may be made from any additional therapeutic agent known to be useful for co-administration with a co-agonist of the NMDAR. The choice of additional therapeutic agent is also dependent upon the particular disease or condition to be treated. Examples of additional therapeutic agents that may be employed in the methods of this invention are those set forth above for use in combination compositions comprising a compound of this invention and an additional therapeutic agent.

In certain embodiments, the combination therapies of this invention include co-administering a compound of Formula I or II and one or more additional therapeutic agents selected from a compound of Formula III, IV, V and VI to a subject in need thereof for treatment of any of the diseases or conditions described herein. In a particular embodiment, the method comprises administering in combination an effective amount of a compound of Formula I and sarcosine. In a further embodiment, the method comprises administering in combination an effective amount of Compound 100 and sarcosine. In a further embodiment, the method comprises administering in combination an effective amount of Compound 103 and sarcosine.

In certain embodiments, the method further comprises administering an antipsychotic therapeutic agent to the subject.

In certain embodiments, the combination therapies of this invention include co-administering a compound of Formula I or II to a patient suffering from schizophrenia who is stable on antipsychotic therapy. In a particular embodiment, the method comprises administering in combination an effective amount of a compound of Formula I or II and a "typical" antipsychotic agent. In another particular embodiment, the method comprises administering in combination an effective amount of a compound of Formula I or II and an "atypical" antipsychotic agent. In a further embodiment, the method comprises administering in combination an effective amount of Compound 100 and an antipsychotic agent. In a further embodiment, the method comprises administering in combination an effective amount of Compound 103 and an antipsychotic agent.

The term "co-administered" or "administering in combination" as used herein means that the additional therapeutic agent may be administered together with a compound of this invention as part of a single dosage form (such as a composition of this invention comprising a compound of the invention and an additional therapeutic agent as described above) or as separate, multiple dosage forms. Alternatively, the additional agent may be administered prior to, consecutively with, or following the administration of a compound of this invention. In such combination therapy treatment, both the compounds of this invention and the additional therapeutic agent(s) are administered by conventional methods. The administration of a composition of this invention, comprising both a compound of the invention and an additional therapeutic agent, to a subject does not preclude the separate administration of that same therapeutic agent, any other additional therapeutic agent or any compound of this invention to said subject at another time during a course of treatment.

Effective amounts of these additional therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the additional therapeutic agent's optimal effective-amount range.

In certain embodiments of any of the foregoing methods, administration of a compound of this invention (e.g., Compound 100) results in reduced nephrotoxicity compared to administration of an equivalent dose of (non-deuterated) D-Serine.

In one embodiment of the invention, where an additional therapeutic agent is administered to a subject, the effective amount of the compound of this invention is less than its effective amount would be where the additional therapeutic agent is not administered. In another embodiment, the effective amount of the additional therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I or Formula II alone or together with one or more of the above-described additional therapeutic agents in the manufacture of a medicament, either as a single composition or as separate dosage forms, for treatment in a subject of a disease, disorder or symptom set forth above. Another aspect of the invention is a compound of Formula I or Formula II for use in the treatment in a subject of a disease, disorder or symptom thereof delineated herein.

Example 1. Evaluation of the Pharmacokinetic Profile of a D-D-Serine (Compound 100)

Evaluation of the Pharmacokinetic Profile of Compound 100 in Male Sprague-Dawley Rats: The hippocampus, cortex and plasma concentration of Compound 100 (92% D by mass spectroscopy) was investigated in male Sprague Dawley rats. The rats were administered a discrete 30 mg/kg PO dose of Compound 100 in 0.5% methylcellulose in water, in the fasted state. The hippocampus, cortex and plasma were collected at 1 hour and 6 hours and analyzed for Compound 100 concentration. The mean plasma, hippocampus and cortex concentration at 1 hour and 6 hours post dose are shown in Table 1 and FIG. 1. The mean plasma, hippocampus, and cortex concentrations at 1 hour were 19200 ng/mL, 674 ng/g, and 754 ng/g, respectively. The mean plasma, hippocampus, and cortex concentrations at 6 hours were 1780 ng/mL, 1385 ng/g, and 936 ng/g, respectively. Similar concentrations of Compound 100 were seen in hippocampus and cortex at 1 hour and 6 hours. Concentrations of Compound 100 in plasma, hippocampus, and cortex were within 2-fold of each other at 6 hour.

TABLE 1

Mean Plasma, Hippocampus and Cortex Concentration at 1 hr and 6 hr and (CV %) for Compound 100 in Male, Sprague-Dawley Rats Following PO Administration of a 30 mg/kg Discrete Dose

| Compound | Dose (mg/kg) | Plasma (ng/mL) | | Hippocampus (ng/g) | | Cortex (ng/g) | |
| --- | --- | --- | --- | --- | --- | --- | --- |
| | | 1 hr | 6 hr | 1 hr | 6 hr | 1 hr | 6 hr |
| Compound 100 | 30 | 19200 (2.2%) | 1780 (20.7%) | 674 | 1385 (0.5%) | 754 (7.9%) | 936 (3.6%) |

Figure 2:
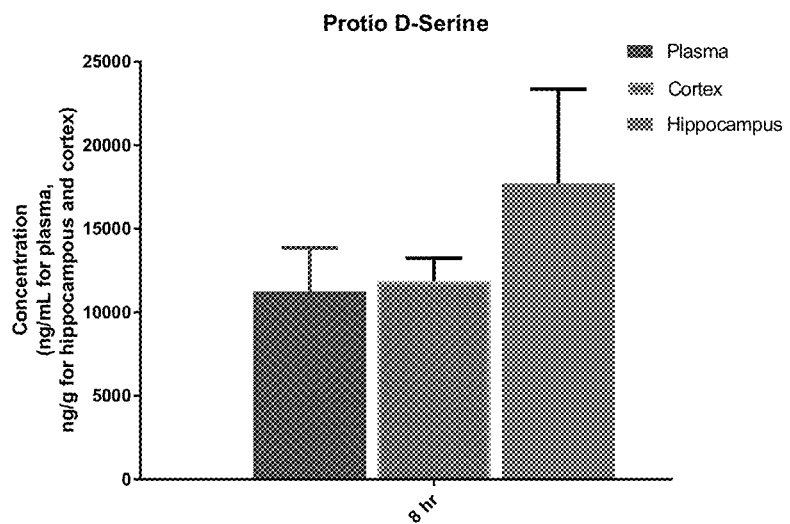
FIG. 2 is a graph showing the concentration of non-deuterated D-serine in rat plasma, hippocampus, and cortex after administration of a single dose of 300 mg/kg.

Example 2. Evaluation of Pharmacokinetics and Nephrotoxicity of Non-Deuterated D-Serine The nephrotoxicity of non-deuterated D-serine was investigated in Male Sprague-Dawley Rats. The rats were administered a discrete dose of 300 mg/kg PO dose of non-deuterated D-serine in 0.5% methylcellulose in water, in the fasted state. The hippocampus, cortex and plasma were collected and analyzed. Additional blood was collected and were analyzed for the full clinical chemistry profile. Urine was also collected and examined for glucose and total protein. The average endogenous level of the non-deuterated D-serine was 155 ng/mL in rat plasma, 8970 ng/g in rat cortex, and 13450 ng/g in rat hippocampus from control group. The endogenous level of non-deuterated D-serine was only subtracted from the reported plasma concentration. The plasma pharmacokinetic (PK) parameters for non-deuterated D-serine are shown in Table 2. The hippocampus, cortex, and plasma concentration at 8 hr for the non-deuterated D-serine are shown in Table 3 and FIG. 2. The $T_{max}$, $T_{1/2}$, $C_{max}$ and $AUC_{inf}$ for non-deuterated D-serine were 0.5 hr, 3.63 hr, 268000 ng/mL, and 500000 hr*ng/mL; respectively. The mean plasma, hippocampus, and cortex concentration at 1 hour are 19200 ng/mL, 674 ng/g, and 754 ng/g; respectively. The mean plasma, hippocampus, and cortex concentrations at 8 hours were 11250 ng/mL, 17725 ng/g, and 11875 ng/g, respectively. Concentrations of non-deuterated D-serine in plasma, hippocampus, and cortex were within 2-fold of each other at 8 hours. Nephrotoxicity of the non-deuterated D-serine at 300 mg/kg in Male Sprague-Dawley Rats was evaluated. Blood urea nitrogen and creatinine levels were elevated. Elevated levels of urea nitrogen and creatinine are suggestive of nephrotoxicity. The presence of glucose was observed in urine.

TABLE 2

Mean Plasma Pharmacokinetic Parameters (CV %) for non-deuterated D-Serine in Male, Sprague-Dawley Rats Following PO Administration of a 300 mg/kg Discrete Dose

| Compound | Dose (mg/kg) | $T_{1/2}$ (hr) | $T_{max}$ (hr) | $C_{max}$ (ng/mL) | $AUC_{inf}$ (hr*ng/mL) |
| --- | --- | --- | --- | --- | --- |
| Non-deuterated D-Serine | 300 | 3.63 (19.6%) | 0.5 | 268000 (26.3%) | 500000 (10.9%) |

TABLE 3

Mean Plasma, Hippocampus and Cortex Concentration at 8 hr and (CV %) for Non-deuterated D-Serine in Male, Sprague-Dawley Rats Following PO Administration of a 300 mg/kg Discrete Dose

| Compound | Route | Dose (mg/kg) | Plasma (ng/mL) 8 hr | Hippocampus (ng/g) 8 hr | Cortex (ng/g) 8 hr |
|---|---|---|---|---|---|
| Non-deuterated D-Serine | PO | 300 | 11250 (23.3%) | 17725 (31.8%) | 11875 (11.5%) |

Figure 3:
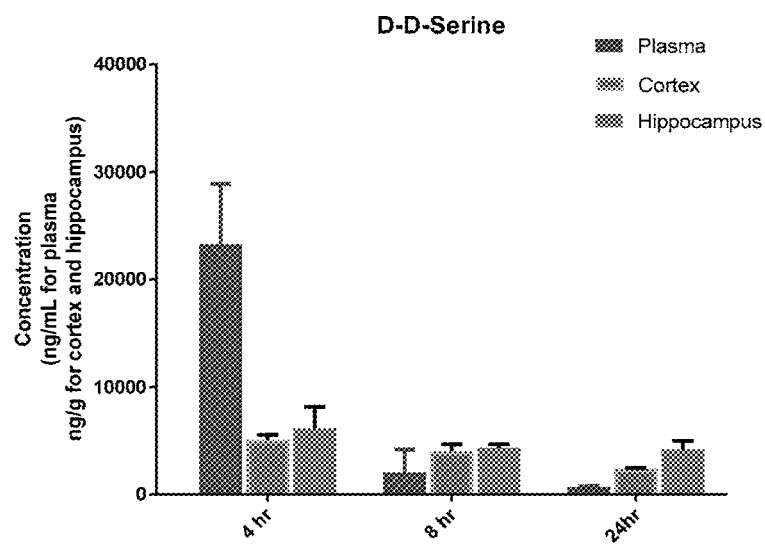
FIG. 3 is a graph showing the concentration of Compound 100 in rat plasma, hippocampus, and cortex after administration of a single dose of 150 mg/kg.
Figure 4:
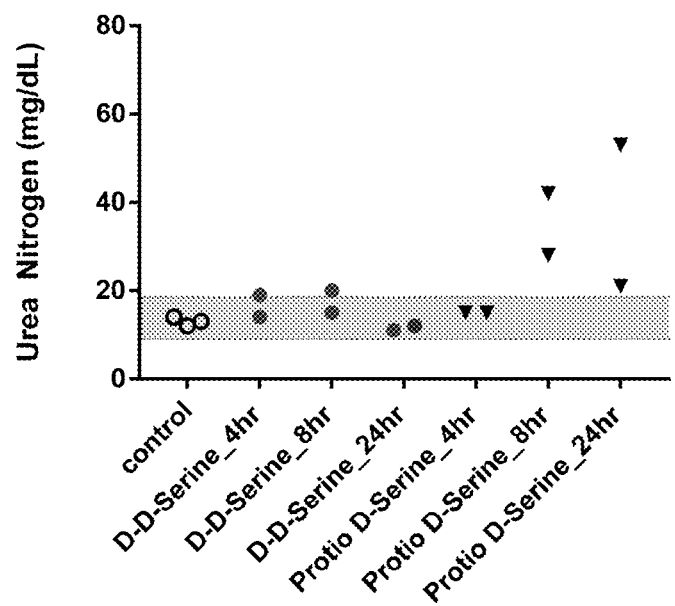
FIG. 4 is a graph showing the urea nitrogen level in rats after administration of a single dose of 150 mg/kg of either Compound 100 or non-deuterated D-serine.
Figure 5:
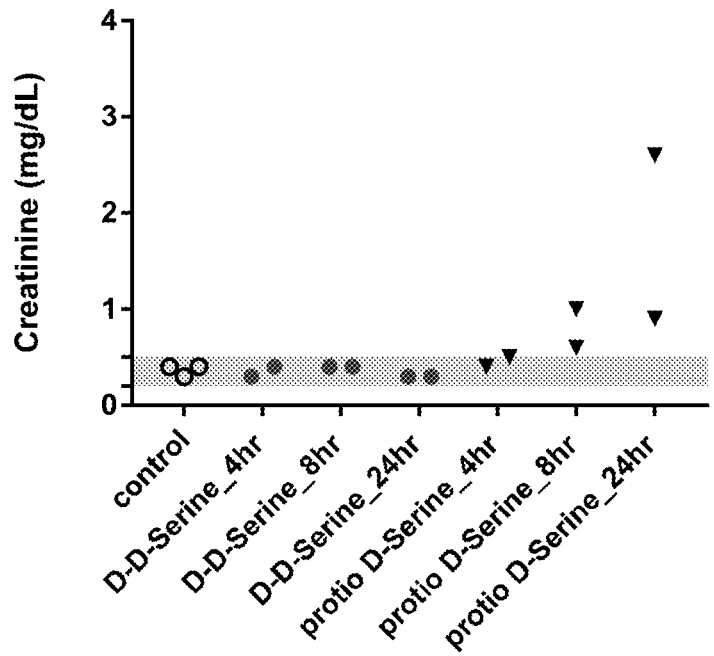
FIG. 5 is a graph showing the creatinine level in rats after administration of a single dose of 150 mg/kg of either Compound 100 or non-deuterated D-serine.
Figure 6:
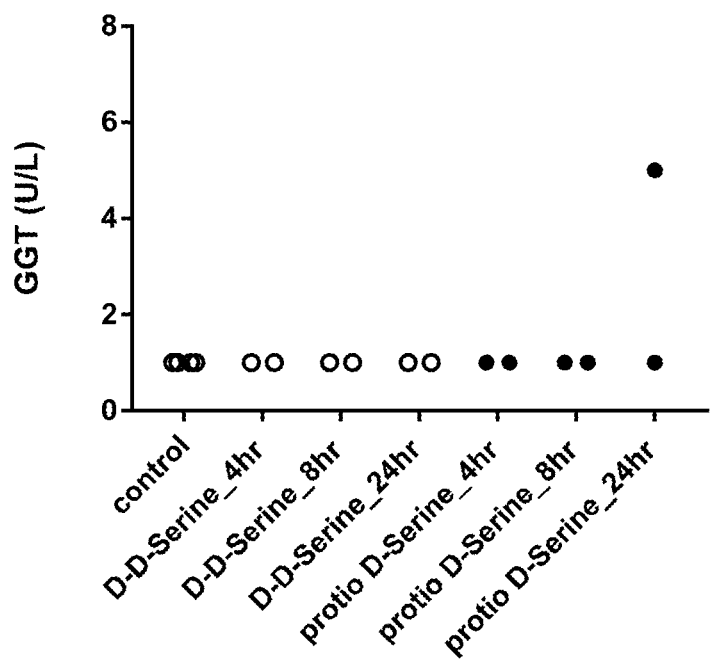
FIG. 6 is a graph showing the GGAT level in rats after administration of a single dose of 150 mg/kg of either Compound 100 or non-deuterated D-serine.
Figure 7:
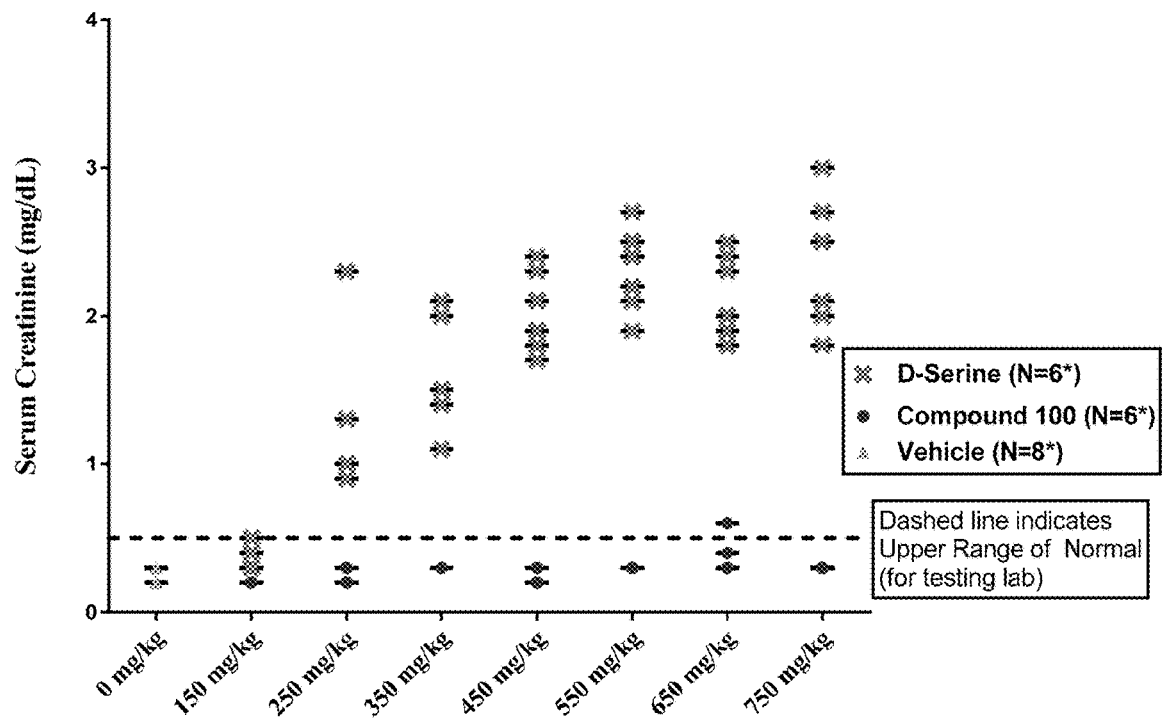
FIG. 7 is a graph showing creatinine levels in rats following PO (oral) administration of non-deuterated D-Serine and deuterated D-Serine (Compound 100).
Figure 8:
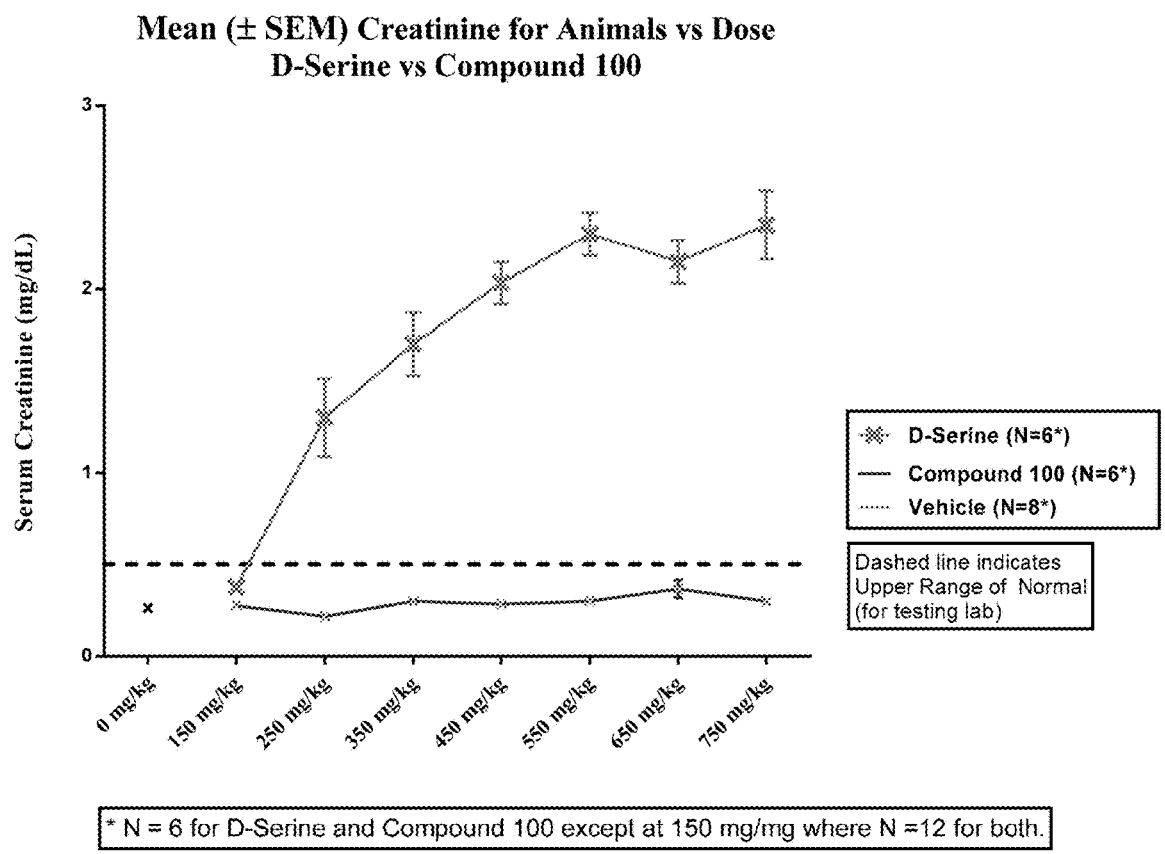
FIG. 8 is a graph showing mean creatinine levels in rats following PO (oral) administration of non-deuterated D-Serine and deuterated D-Serine (Compound 100).
Figure 9:
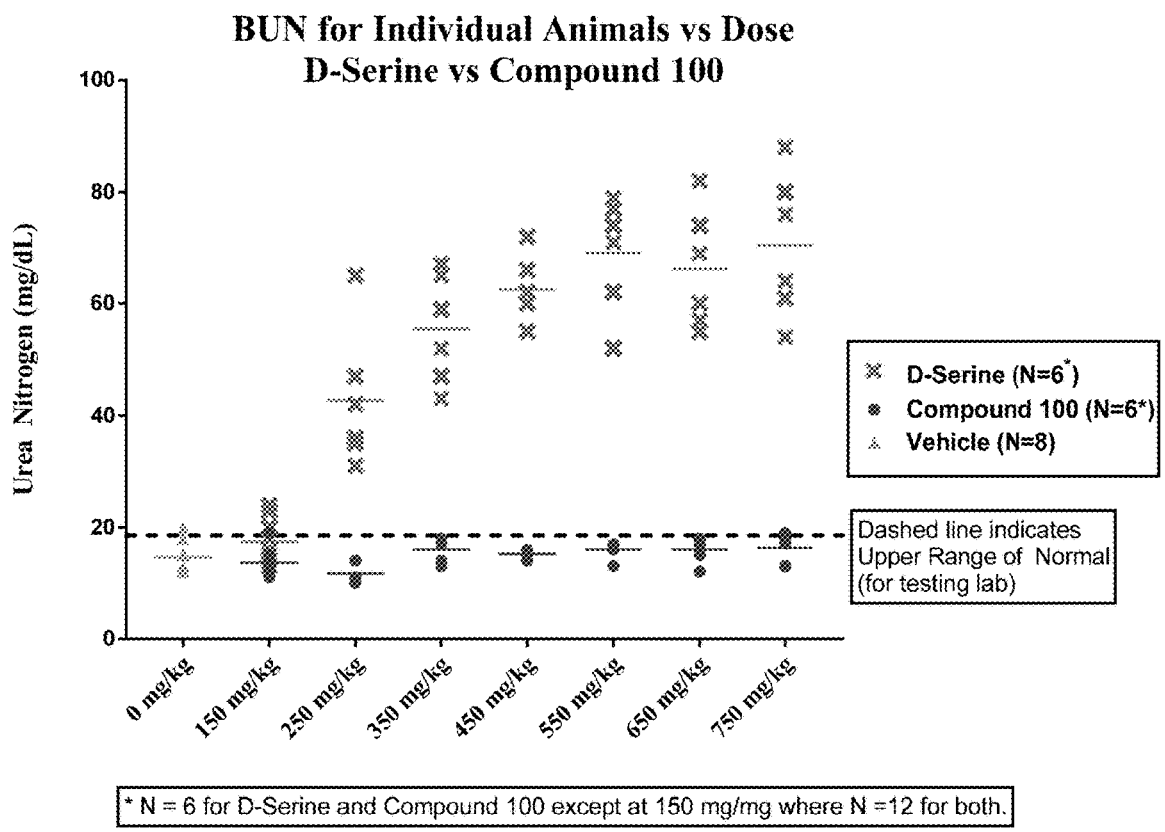
FIG. 9 is a graph showing urea nitrogen (BUN) level in rats following PO (oral) administration of non-deuterated D-Serine and deuterated D-Serine (Compound 100).
Figure 10:
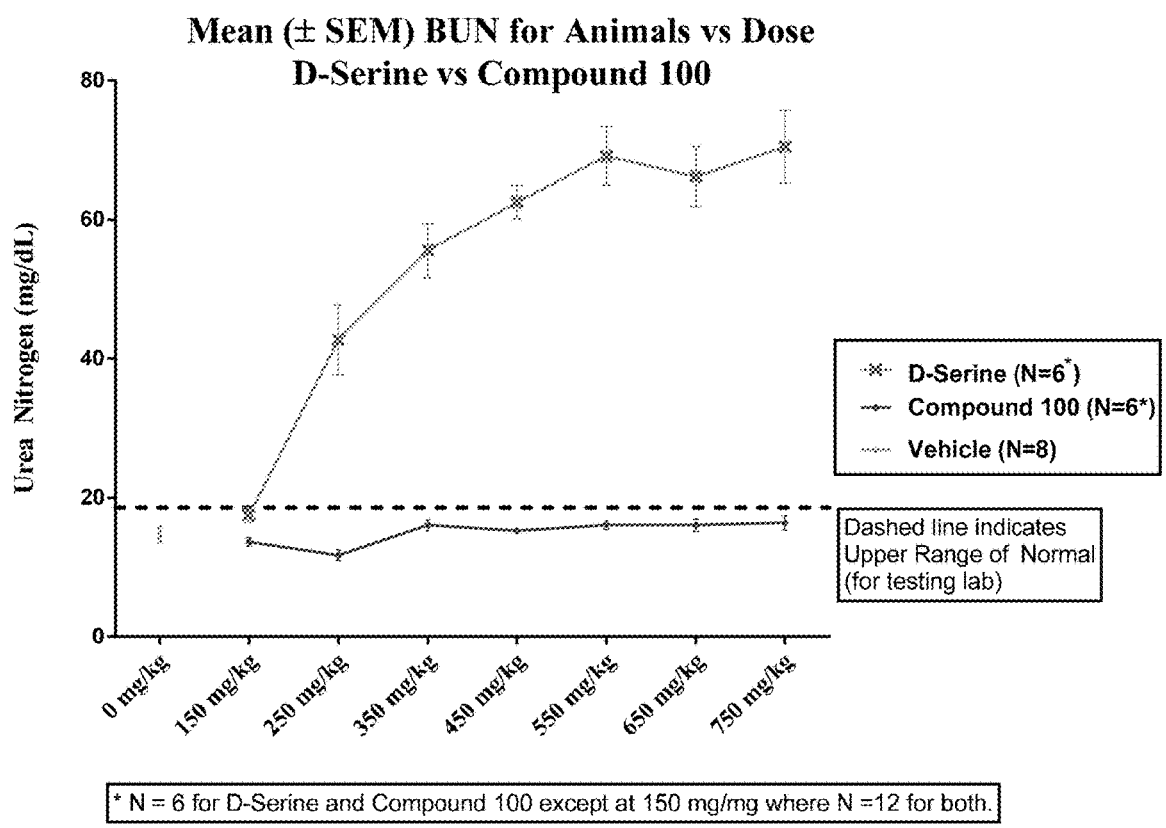
FIG. 10 is a graph showing mean urea nitrogen (BUN) level in rats following PO (oral) administration of non-deuterated D-Serine and deuterated D-Serine (Compound 100).

Example 3. Evaluation of Pharmacokinetics Profile and Nephrotoxicity of Compound 100 and Non-Deuterated D-Serine The pharmacokinetic profile of Compound 100 was investigated in male Sprague-Dawley rats compared with that of non-deuterated D-serine. The rats were administered discrete 150 mg/kg PO doses of Compound 100 (92% D by mass spectroscopy) in 0.5% methylcellulose in water and non-deuterated D-serine, in the fasted state. Plasma was collected and analyzed for Compound 100 and non-deuterated D-Serine. Additional blood was collected and analyzed for the full clinical chemistry profile. The PK parameters for Compound 100 and non-deuterated D-serine are shown in Table 4. The hippocampus, cortex, and plasma concentration at 4 hr, 8 hr, and 24 hr for Compound 100 are shown in Table 5 and FIG. 3. Clinical pathology data are shown in FIGS. 4, 5 and 6.

In rats administered a single 150 mg/kg discrete PO dose of each compound, the $T_{max}$ for Compound 100 was 2-fold greater than that of the non-deuterated D-serine. The $C_{max}$ and $AUC_{inf}$ for Compound 100 were similar to the non-deuterated D-serine. The $T_{max}$, $C_{max}$ and AUCs for non-deuterated D-serine were 0.333 hr, 180000 ng/mL, and 349000 hr*ng/mL; respectively. The $T_{max}$, $C_{max}$ and $AUC_{inf}$ for Compound 100 were 0.667 hr, 186000 ng/mL, and 383000 hr*ng/mL, respectively. The mean plasma, hippocampus, and cortex concentrations at 4 hr were 23283 ng/mL, 6155 ng/g, and 5070 ng/g, respectively. The mean plasma, hippocampus, and cortex concentrations at 8 hr were 2038 ng/mL, 4335 ng/g, and 4035 ng/g, respectively. The mean plasma, hippocampus, and cortex concentrations at 24 hr were 711 ng/mL, 4200 ng/g, and 2420 ng/g, respectively. Compound 100 concentrations in plasma and cortex decreased within 24 hr; however, Compound 100 concentration in hippocampus remained steady at 24 hr.

The nephrotoxicity of Compound 100 and non-deuterated D-serine were evaluated in male Sprague-Dawley Rats. Rats received 150 mg/kg of either Compound 100 or non-deuterated D-serine (PO administration). Elevated levels of blood urea nitrogen (BUN) were seen in the non-deuterated D-serine at 8 hr and 24 hr serum samples. Elevated levels of creatinine and Gamma glutamyl transferase (GGT) were seen in the non-deuterated D-serine at 24 hr serum samples. Elevated levels of blood urea nitrogen, creatinine and GGT are suggestive of nephrotoxicity. In contrast, with Compound 100, levels of urea nitrogen, creatinine, and GGT level at 4, 8, and 24 hours were similar in comparison to control values and reference values provided by Charles River Laboratory. While non-deuterated D-serine caused an increase in levels of biomarkers of nephrotoxicity, administration of Compound 100 did not increase levels of biomarkers of nephrotoxicity.

TABLE 4

Mean Plasma Pharmacokinetic Parameters (CV %) for non-deuterated D-Serine and Compound 100 in Male, Sprague-Dawley Rats Following PO Administration of a 150 mg/kg Discrete Dose

| Compound | Dose (mg/kg) | $T_{max}$ (hr) | $C_{max}$ (ng/mL) | $AUC_{inf}$ (hr*ng/mL) |
|---|---|---|---|---|
| Non-deuterated D-Serine | 150 | 0.333 (38.7%) | 180000 (20.9%) | 349000 (29.4%) |
| Compound 100 | 150 | 0.667 (38.7%) 2.0X | 186000 (24.7%) | 383000 (10.5%) |

TABLE 5

Mean Plasma, Hippocampus and Cortex Concentration at 4 hr, 8 hr, 24 hr and CV % for Compound 100 in Male, Sprague-Dawley Rats Following PO Administration of a 150 mg/kg Discrete Dose

| Compound | Route | Dose (mg/kg) | Time | Plasma (ng/mL) | Hippocampus (ng/g) | Cortex (ng/g) |
|---|---|---|---|---|---|---|
| Compound 100 | PO | 150 | 4 hr | 23283 (24.1%) | 6155 (32.5%) | 5070 (9.5%) |
| | | | 8 hr | 2038 (105%) | 4335 (8%) | 4035 (15.6) |
| | | | 24 hr | 711 (8.9%) | 4220 (18.5%) | 2420 (1.8%) |

Additional experiments were performed to compare the nephrotoxicity of Compound 100 (Compound 100) and non-deuterated D-serine at doses from 150 mg/kg to 750 mg/kg. The results are shown in FIGS. 7-10. It can be seen from FIGS. 7-10 that minimal changes in BUN or creatinine were observed in animals dosed with Compound 100, while animals receiving comparable doses of non-deuterated D-serine showed increasingly elevated levels of BUN and creatinine. During the dose escalation, the exposure as measured by AUC and $C_{max}$ were greater for Compound 100, yet the gross signs of nephrotoxicity were only observed in rats receiving non-deuterated D-serine (not Compound 100).

Figure 11:
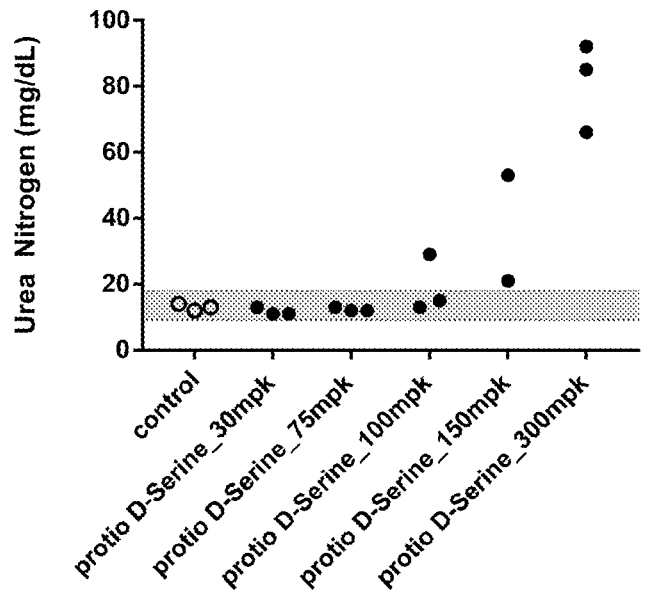
FIG. 11 is a graph showing the urea nitrogen level in rats after administration of various dosages of non-deuterated D-serine.
Figure 12:
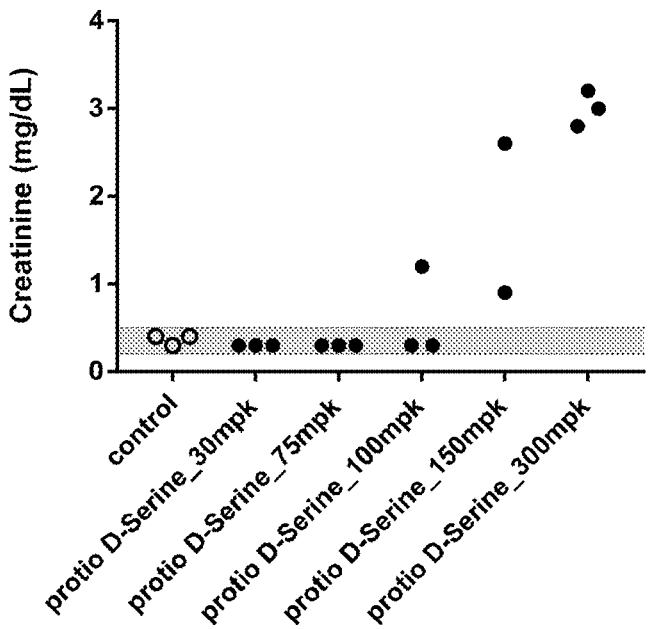
FIG. 12 is a graph showing the creatinine level in rats after administration of various dosages of non-deuterated D-serine.
Figure 13:
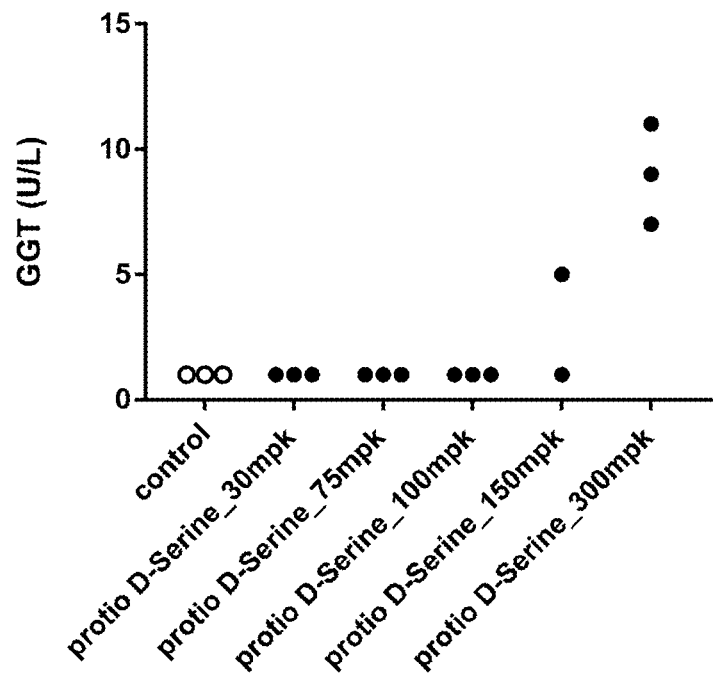
FIG. 13 is a graph showing GGAT level in rats after administration of various dosages of non-deuterated D-serine.

Example 4. Evaluation of the Pharmacokinetics and Nephrotoxicity Dose Response for Non-Deuterated D-Serine in Male Sprague-Dawley Rats The pharmacokinetic profile of non-deuterated D-serine was investigated in male Sprague-Dawley rats. The rats were administered a single discrete 30, 75, 100, 150, and 300 mg/kg PO doses of non-deuterated D-serine in 0.5% methylcellulose in water, in the fasted state. Plasma was collected and analyzed for the non-deuterated D-serine. Additional blood was collected and analyzed for the full clinical chemistry profile. The PK parameters for the non-deuterated D-Serine are shown in Table 6. Clinical pathology data are shown in FIGS. 11, 12, and 13.

In rats administered a single discrete 30, 75, 100, 150, and 300 mg/kg PO dose of non-deuterated D-serine, the $T_{max}$ was from 0.3 to 0.5 for all doses. Increase in exposure in terms of $C_{max}$ and $AUC_{inf}$ was seen as the doses increased from 30 to 300 mg/kg. The $C_{max}$ for 30, 75, 100, 150, and 300 mg/kg are 24300, 54300, 96100, 180000, and 216000 ng/mL, respectively. The $AUC_{inf}$ for 30, 75, 100, 150, and 300 mg/kg are 50600, 148000, 246000, 349000, and 911000 ng*hr/mL; respectively.

The nephrotoxicity dose response of non-deuterated D-serine was evaluated in male Sprague-Dawley Rats at 30, 75, 100, 150, and 300 mg/kg PO. Elevated levels of urea nitrogen, creatine, and gamma glutamyl transferase (GGT) (which are markers indicative of nephrotoxicity) were seen in the 24 hr samples at the 150 and 300 mg/kg doses compared to control values and reference values provided by Charles River Laboratory.

TABLE 6

Mean Plasma Pharmacokinetic Parameters (CV %) for non-deuterated D-Serine in Male, Sprague-Dawley Rats Following PO Administration of 30, 75, 100, 150, and 300 mg/kg Discrete Dose

| Compound | Dose (mg/kg) | $T_{max}$ (hr) | $C_{max}$ (ng/mL) | $AUC_{inf}$ (ng*h/mL) |
| --- | --- | --- | --- | --- |
| Non-deuterated D-Serine | 30 | 0.5 | 24300 (10%) | 50600 (9.9%) |
| Non-deuterated D-Serine | 75 2.5X | 0.5 | 54300 (13.2%) 2.2X | 148000 (14.3%) 2.9X |
| Non-deuterated D-Serine | 100 3.3X | 0.5 | 96100 (40.4%) 4.0X | 246000 (29.4%) 4.9X |
| Non-deuterated D-Serine | 150 5X | 0.3 (38.7%) | 180000 (20.9%) 7.4X | 349000 (29.4%) 6.9X |
| Non-deuterated D-Serine | 300 10X | 0.5 | 261000 (32.3%) 10.7X | 911000 (6.9%) 18X |

Example 5. Evaluation of the Pharmacokinetics of Deuterated and Non-Deuterated D-Serine in Male Sprague-Dawley Rats

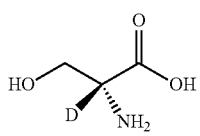

Compound 100

Non-deuterated D-serine and deuterated D-serine (Compound 100) were administered to male Sprague Dawley rats (intravenous (IV), 5 mg/kg in phosphate-buffered saline (PBS); and orally (PO), 10 mg/kg, 0.5% methylcellulose in water). Three rats were used for each group. Blood was collected at the following time points: for IV dosing: pre-dose, 0.05, 0.167, 0.5, 1, 2, 4, 6, 8 and 12 hours post-dose; for PO dosing: pre-dose, 0.25, 0.5, 1, 2, 4, 6, 8 and 12 hours post-dose PO. Urine was collected at pre-dose (minimum 12 hours), 0-6, 6-12 and 12-24 hours. Plasma samples were analyzed and quantified for dosed compound LC-MS/MS.

The results are shown in Table 7:

TABLE 7

| Compound | Route | Dose (mg/kg) | Formulation | $T_{1/2}$ (hr) | $T_{max}$ (hr) | $C_{max}$ (ng/mL) | $AUC_{inf}$ (ng*h/mL) |
| --- | --- | --- | --- | --- | --- | --- | --- |
| Non-deuterated D-serine | PO | 10 | 0.5% Methylcellulose | 1.77 | 0.417 | 8780 | 13200 |
| Compound 100 | PO | 10 | 0.5% Methylcellulose | 2.66 | 0.417 | 11400 | 21500 |

It was found that deuterated D-serine (Compound 100) had a half-life ($T_{1/2}$) about 1.5-fold longer than for the non-deuterated D-serine; the deuterated and non-deuterated compounds had a similar $T_{max}$. Deuterated D-serine (Compound 100) had a $C_{max}$ about 1.3-fold greater than for the non-deuterated D-serine, and an $AUC_{inf}$ about 1.6-fold greater than for the non-deuterated D-serine.

In a separate experiment, non-deuterated D-serine and two deuterated D-serine analogs (Compound 100 and Compound 103 (96% D)) were administered to male Sprague Dawley rats.

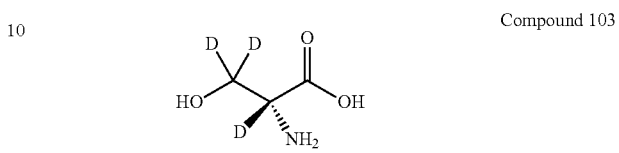

Compound 103

The results showed that Compound 100 and Compound 103 had similar PK parameters.

Example 6. Exemplary Formulation of a D-D-Serine

A modified-release tablet formulation of a D-D-serine is prepared using the materials shown in the table below:
Tablet Strength: 500 mg D-D-serine (e.g., Compound 100)
Total Tablet Wt: 855 mg

| Material | Generic Name | Wt % | Amount per tablet (mg) |
| --- | --- | --- | --- |
| D-D-Serine | N/A | 58.5 | 500.0 |
| Methocel K100M | Hypromellose | 30.0 | 256.5 |
| Vivapur 101 | Microcrystalline cellulose | 10.0 | 85.7 |
| Aerosil 200 | Colloidal silicon dioxide | 0.5 | 4.3 |
| Magnesium stearate | N/A | 1.0 | 8.6 |
| Total | | 100 | 855 |

Example 7. (2R)-2-Amino-2-Deutero-3-Hydroxy-Propanoic Acid (Compound 100)

The detailed synthesis of racemic 2-amino-2-deutero-3-hydroxy-propanoic acid followed by resolution to obtain (2R)-2-amino-2-deutero-3-hydroxy-propanoic acid (Compound 100) in high e.e. (enantiomeric excess) and with high % D is shown in Scheme 2 below.

Scheme 2

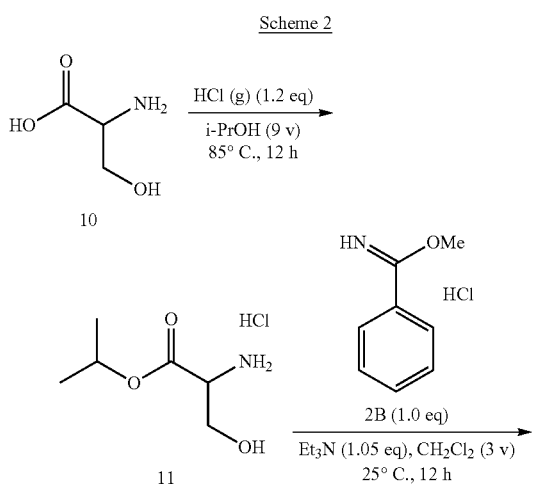

41

-continued

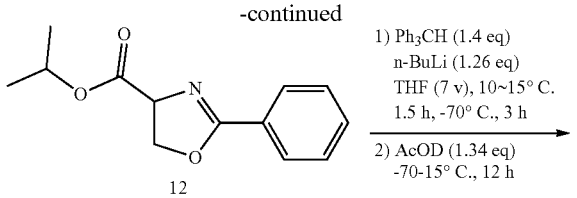

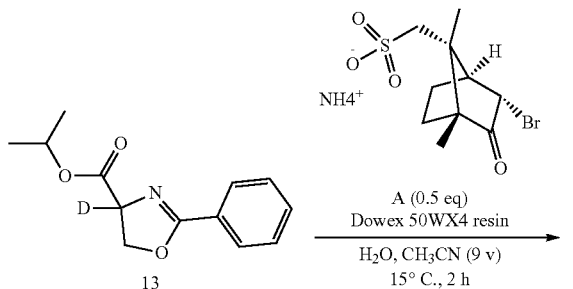

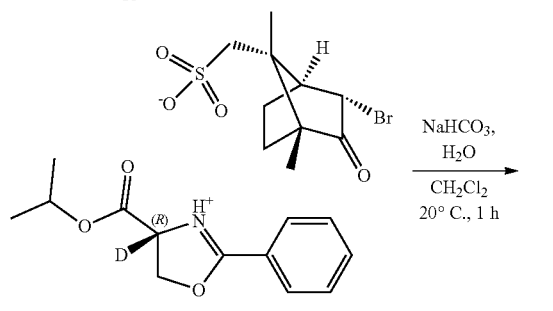

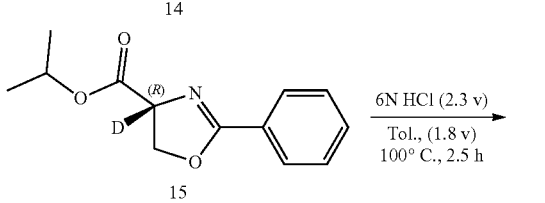

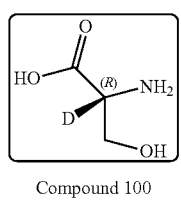

Compound 100

As depicted in Scheme 2, Compound 100 was prepared from non-deuterated D,L-serine. Proton NMR and mass spectral data were consistent with the structure shown above for Compound 100: MS (M+H): 107.2; MS (M−H): 105.2; $^1$H-NMR (400 MHz, D$_2$O): δ 3.90 (dd, J$_1$=12.4 Hz, J$_2$=19.2 Hz, 2H). Deuterium incorporation was determined by proton NMR to be approximately 96%. SFC (supercritical fluid chromatography) analysis of the benzyloxycarbonylamino derivative of Compound 100 revealed no trace of the S-enantiomer.

Example 8. (2R)-2-Amino-2,3,3-Trideutero-3-Hydroxy-Propanoic Acid (Compound 103)

The details of the resolution of commercially available racemic 2-amino-2,3,3-trideutero-3-hydroxy-propanoic acid to obtain (2R)-2-amino-2,3,3-tri-deutero-3-hydroxy-propanoic acid (Compound 103) in high e.e. and with high % D are shown in Scheme 3 below.

42

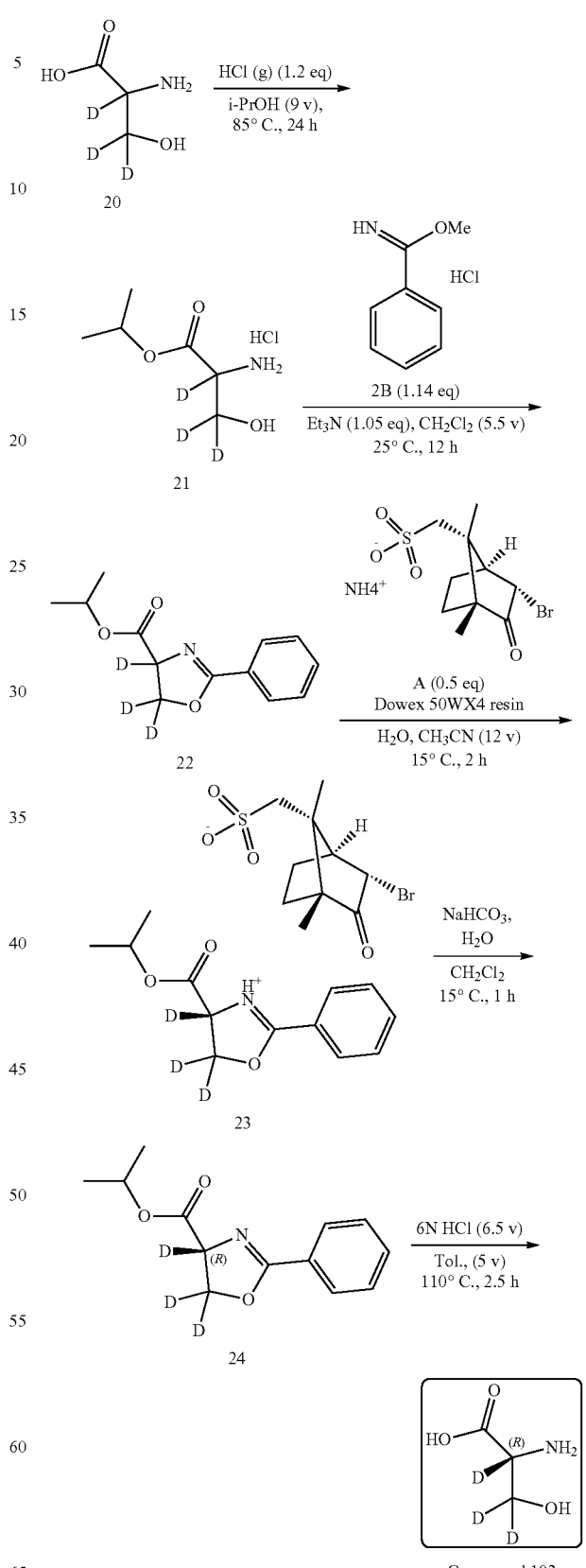

As depicted in Scheme 3, Compound 103 was obtained by resolution of commercially available racemic 2-amino-2,3, 3-trideutero-3-hydroxy-propanoic acid. Proton NMR and mass spectral data were consistent with the structure shown above for Compound 103: MS (M+H): 109.2; $^1$H-NMR (400 MHz, D20): deuterium incorporation was determined by proton NMR of a precursor and a derivative to be approximately 96% at the methinyl position; deuterium incorporation at the methylenyl position is approximately 98% (based on the stated purity of a precursor). SFC (supercritical fluid chromatography) analysis of the benzyloxycarbonylamino derivative of Compound 103 revealed no trace of the S-enantiomer.

Example 9. Evaluation of the Pharmacology of Compound 100 and Non-Deuterated D-Serine in an Automated Patch Clamp System (ScreenPatch©)

The activation of the NMDA receptors by Compound 100 and by D-serine was assessed in an automated patch clamp system (ScreenPatch©) using HEK293 cells expressing human NMDAR subunits GluN1 and GluN2A.

Cells were treated with increasing concentrations of Compound 100 or d-serine (0.003 to 10 µM). Peak current and steady state current were measured. The activity at the NMDA receptor was indistinguishable for the two compounds. The binding and activation of receptors by D-serine and Compound 100 were similar in all cases where measured. Compared to the non-deuterated compound, Compound 100 demonstrated nearly identical in vitro binding affinity for the glycine modulatory site of NMDAR. For the binding affinity of Compound 100 to the glycine site of NMDA receptor from rat cerebral cortical membranes, the average $K_i$ for Compound 100 was 0.91 µM while the average $K_i$ for D-serine was 0.95 µM.

Figure 14:
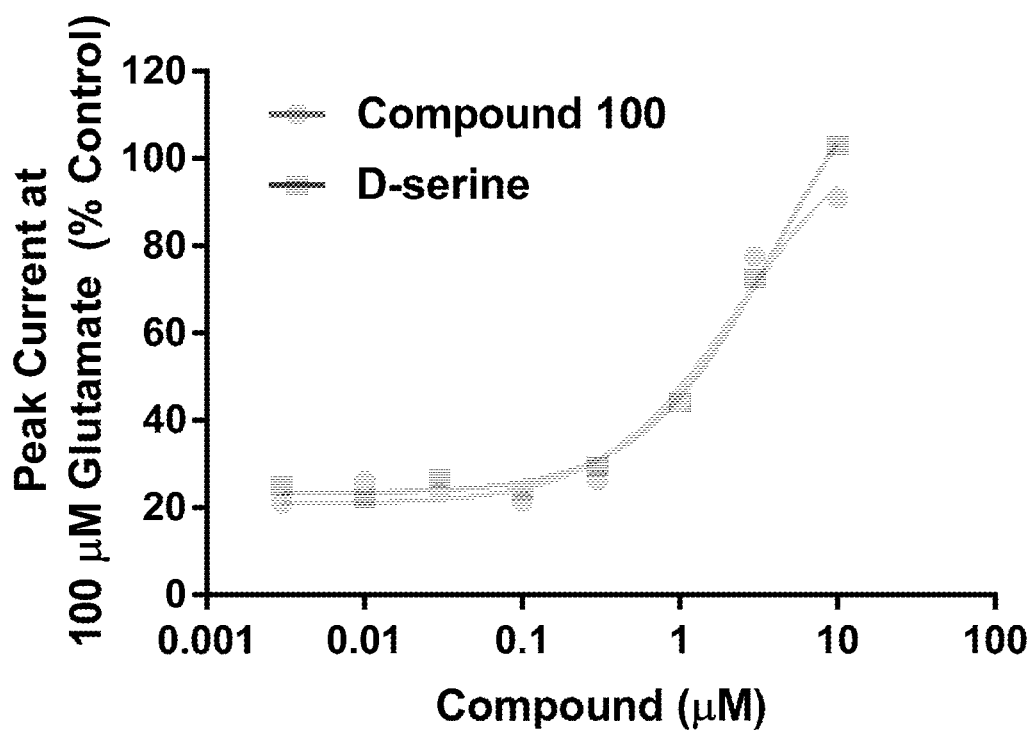
FIG. 14 is a line plot showing NMDA receptor activity for non-deuterated ("Protio") D-serine and compound 100 in an automated patch clamp system.

A representative graph is depicted in FIG. 14.

Example 10. Evaluation of the Brain Distribution of Compound 100 in Sprague Dawley Rats after PO Administration The distribution profile of Compound 100 was investigated in male Sprague-Dawley rats. The rats (4) were administered a single dose of Compound 100 (oral (PO)) at 100 mg/kg. At 24 hours after dosing, tissues from perfused brain and plasma were collected and analyzed by LC-MS. The concentration of Compound 100 in the cortex (location of the target of interest) was found to be greater than in plasma or other brain locations.

Figure 15:
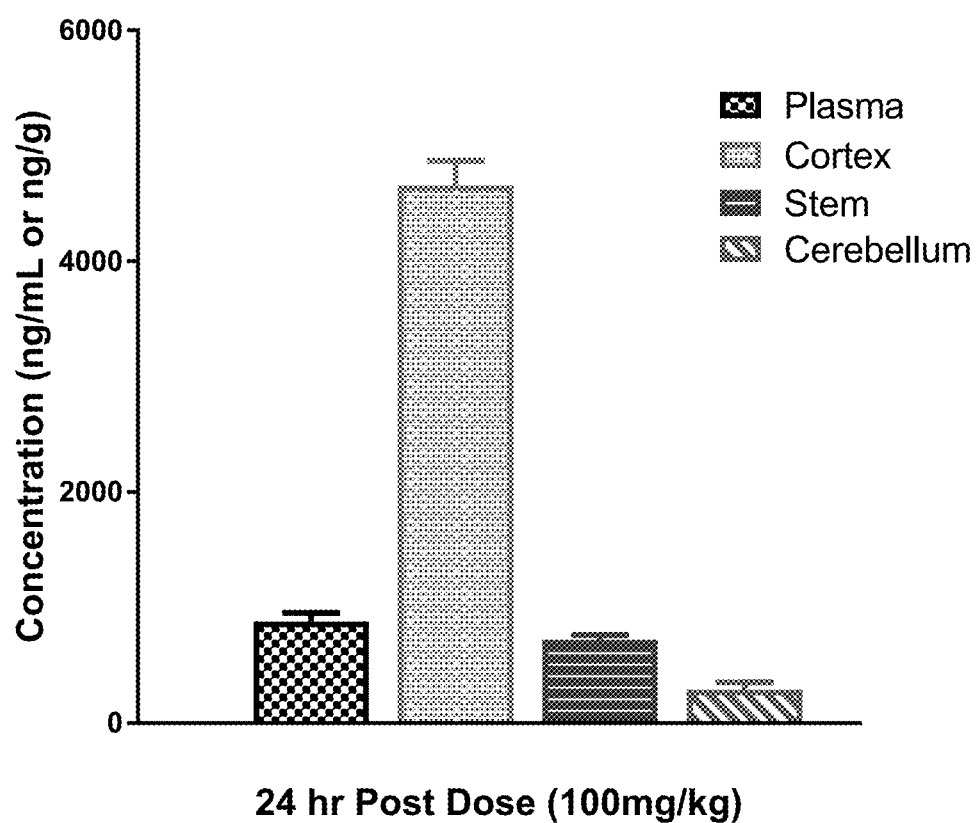
FIG. 15 is a bar graph showing accumulation of compound 100 in the brains of Sprague-Dawley rats.

The plasma, cortex, brain stem, and cerebellum concentration at 24 hr for Compound 100 are shown in FIG. 15.

The mean concentrations at 24 hr in the plasma, cortex, brain stem, and cerebellum were 880 ng/mL, 4660 ng/g, 721 ng/g, and 290 ng/g, respectively.

Example 11. Evaluation of the Concentration of Compound 100 in Sprague Dawley Rats Cortex Versus Plasma after 4 Days of PO Administration Three groups each of 4 male Sprague-Dawley rats were administered a single dose per day of Compound 100 (oral (PO)) at 100 mg/kg for a total of 4 days. After 4 days, tissues from perfused brain and plasma were collected and analyzed by LC-MS at 24 hours (group 1), 72 hours (group 2) and 120 hours (group 3) after dosing.

Figure 16:
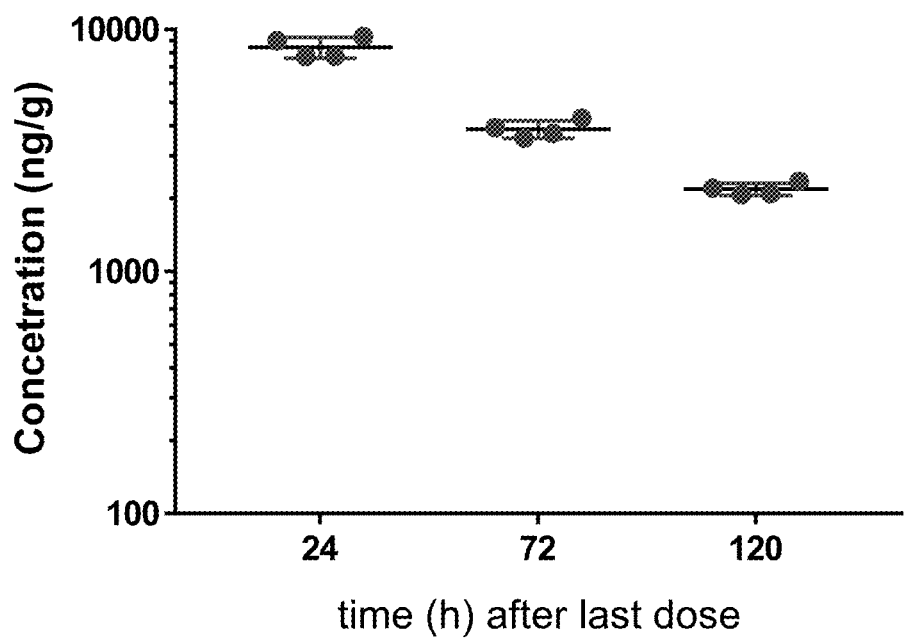
FIG. 16 is a plot showing compound 100 concentration in the brains of Sprague-Dawley rats after 4 days of dosing.

The concentration of Compound 100 in the rat cortex versus time after 4 days of dosing 100 mg/kg is shown in FIG. 16.

Based on the concentration versus time data, the half-life ($T_{1/2}$) of Compound 100 in the cortex (location of the target) was shown to be approximately 48 hours, in contrast to the much shorter plasma $T_{1/2}$ which was shown to be less than 12 hours. This result illustrates that the systemic PK is decoupled from the brain PK making Compound 100 a surprisingly valuable compound for the treatment of diseases that benefit from NMDAR activation (or increases in D-serine).

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

We claim:

1. A method of treating epilepsy, NMDAR encephalitis, Parkinson's disease, cognitive deficits in Parkinson's disease, Alzheimer's disease, mild cognitive impairment, amyotrophic lateral sclerosis (ALS), Huntington's disease, bipolar disorder, bipolar mania, bipolar depression, treatment-refractory depression, cognitive deficits in depression, major depressive disorder, generalized anxiety disorder, major depressive disorder with mixed features, and cognition deficits associated with Huntington's disease, subjective cognitive decline, traumatic brain injury, or Lewy Body Dementia, the method comprising administering to a subject in need thereof an effective amount of Compound 100:

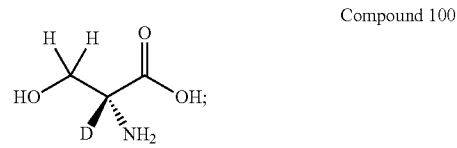

Compound 100 wherein each position designated specifically as deuterium has at least 90% incorporation of deuterium; and wherein the compound is at least about 90% stereomerically pure;

or a pharmaceutically acceptable salt thereof.

2. The method of claim 1, wherein the method is for treating NMDAR encephalitis, the method comprising administering to a subject in need thereof an effective amount of Compound 100;

wherein each position designated specifically as deuterium has at least 90% incorporation of deuterium; and wherein the compound is at least about 90% stereomerically pure;

or a pharmaceutically acceptable salt thereof.

3. A method of treating depression, the method comprising administering to a subject in need thereof an effective amount of
Compound 100:

Compound 100

$$\text{HO-}\overset{\text{H}}{\underset{\text{D}}{\text{C}}}\text{-}\overset{\text{H}}{\underset{\text{NH}_2}{\text{C}}}\text{-}\overset{\text{O}}{\text{C}}\text{-OH;}$$

wherein each position designated specifically as deuterium has at least 90% incorporation of deuterium; and wherein the compound is at least about 90% stereomerically pure;
or a pharmaceutically acceptable salt thereof.

4. A method of increasing NMDA receptor function, the method comprising contacting a cell with
Compound 100:

Compound 100

$$\text{HO-}\overset{\text{H}}{\underset{\text{D}}{\text{C}}}\text{-}\overset{\text{H}}{\underset{\text{NH}_2}{\text{C}}}\text{-}\overset{\text{O}}{\text{C}}\text{-OH;}$$

wherein each position designated specifically as deuterium has at least 90% incorporation of deuterium; and wherein the compound is at least about 90% stereomerically pure;
or a pharmaceutically acceptable salt thereof, such that NMDA receptor function in the cell is increased.

5. The method of claim 1, wherein in Compound 100, the position designated specifically as deuterium has at least 95% incorporation of deuterium.

6. The method of claim 5, wherein in Compound 100, the position designated specifically as deuterium has at least 97% incorporation of deuterium.

7. The method of claim 1, wherein in Compound 100, any atom not designated as deuterium is present at its natural isotopic abundance.

8. The method of claim 1, wherein Compound 100 is administered orally.

9. The method of claim 1, wherein the method comprises administering Compound 100 in an amount from 1 to 10 g/day.

10. The method of claim 1, wherein in Compound 100, less than 2% of the enantiomer of Compound 100 is present.

11. The method of claim 9, wherein the method comprises administering Compound 100 in an amount from 1 to 5 g/day.

12. The method of claim 1, wherein Compound 100 is administered in a unit dose form in an amount from 1 g to 10 g.

13. The method of claim 12, wherein Compound 100 is administered in a unit dose form in an amount of about 1 g, about 2 g, about 3 g, about 4 g, about 5 g, about 8 g or about 10 g.

14. The method of claim 5, wherein Compound 100 is administered orally.

15. The method of claim 5, wherein the method comprises administering Compound 100 in an amount from 1 to 10 g/day.

16. The method of claim 5, wherein in Compound 100, less than 2% of the enantiomer of Compound 100 is present.

17. The method of claim 15, wherein the method comprises administering Compound 100 in an amount from 1 to 5 g/day.

18. The method of claim 5, wherein Compound 100 is administered in a unit dose form in an amount from 1 g to 10 g.

19. The method of claim 18, wherein Compound 100 is administered in a unit dose form in an amount of about 1 g, about 2 g, about 3 g, about 4 g, about 5 g, about 8 g or about 10 g.

20. The method of claim 6, wherein Compound 100 is administered orally.

21. The method of claim 6, wherein the method comprises administering Compound 100 in an amount from 1 to 10 g/day.

22. The method of claim 6, wherein in Compound 100, less than 2% of the enantiomer of Compound 100 is present.

23. The method of claim 21, wherein the method comprises administering Compound 100 in an amount from 1 to 5 g/day.

24. The method of claim 6, wherein Compound 100 is administered in a unit dose form in an amount from 1 g to 10 g.

25. The method of claim 24, wherein Compound 100 is administered in a unit dose form in an amount of about 1 g, about 2 g, about 3 g, about 4 g, about 5 g, about 8 g or about 10 g.

\* \* \* \* \*